United States Patent
Elworthy et al.

(10) Patent No.: US 6,849,657 B2
(45) Date of Patent: Feb. 1, 2005

(54) 2-PYRROLIDONE DERIVATIVES AS PROSTANOID AGONISTS

(75) Inventors: Todd Richard Elworthy, Los Gatos, CA (US); Michael Garret Roepel, San Francisco, CA (US); David Bernard Smith, San Mateo, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/197,279

(22) Filed: Jul. 16, 2002

(65) Prior Publication Data

US 2003/0064964 A1 Apr. 3, 2003

Related U.S. Application Data

(60) Provisional application No. 60/305,762, filed on Jul. 16, 2001.

(51) Int. Cl.$^7$ .................. A61K 31/4015; C07D 207/12
(52) U.S. Cl. ...................... 514/424; 548/550; 548/551
(58) Field of Search ................. 548/551, 550; 514/424

(56) References Cited

U.S. PATENT DOCUMENTS

| | | | |
|---|---|---|---|
| 3,975,399 | A | 8/1976 | DeFranco et al. |
| 4,113,873 | A | 9/1978 | Himizu et al. |
| 4,115,401 | A | 9/1978 | Nanthavong et al. |
| 4,177,346 | A | 12/1979 | Nelson |
| 4,320,136 | A | 3/1982 | Scribner |
| 6,211,226 | B1 | 4/2001 | Hellberg et al. |

FOREIGN PATENT DOCUMENTS

| | | |
|---|---|---|
| BE | 841165 | 10/1976 |
| EP | 1 097 922 A1 | 5/2001 |
| EP | 1 132 086 A | 9/2001 |
| GB | 1553595 | 10/1979 |
| GB | 1569982 | 6/1980 |
| GB | 1583163 | 1/1981 |
| WO | WO 99 02164 A | 1/1999 |
| WO | WO 00/21532 A1 | 4/2000 |
| WO | WO 00/21542 A1 | 4/2000 |
| WO | WO 01/46140 A1 | 6/2001 |
| WO | WO 01 62724 A | 8/2001 |
| WO | WO 02/24647 A1 | 3/2002 |
| WO | WO 02/42268 A2 | 5/2002 |

OTHER PUBLICATIONS

Zoretic et al., "Synthesis of (E)–7–[[2–[4(m–Trifluoromethylphenoxy)–3α and 3β–Hydroxy–1–butenyl]–5–oxo–1–pyrrolidinyl]]heptanoic Acids", *J. Heterocyclic Chem.*, Mar.–Apr. 1983, pp. 465–466, 20.

Saijo, et al., "Heterocyclic prostaglandins. IV. Synthesis of 8–aza–11–deoxyprostaglandin $E_1$ and its related compounds," *Yakugaku Zashi*, 1980, pp. 389–395, 100(4), Abstract CA 93:204109x.

Suda, et al., "Prostaglandin E Receptor Subtypes in Mouse Osteoblastic Cell Line," *Endocrinology*, 1996, pp. 1698–1705, 137, No. 5.

Suzawa, et al., "The Role of Prostaglandin E Receptor Subtypes (EP1, EP2, EP3, and EP4) in Bone Resorption: An Analysis Using Specific Agonists for the Respective EPs," *Endocrinology*, 2000, pp. 1554–1559, 141(4).

Ono, et al., "Important role of $EP_4$, a subtype of prostaglandin (PG) E receptor, in osteoclast–like cell formation from mouse bone marrow cells induced by $PGE_2$," *Journal of Endocrinology*, 1998, pp. R1–R5, 158.

Hazato, et al., "Synthesis of Thiaprostaglandin $E_1$ Derivatives," *Chem. Pharm. Bull.*, 1985, pp. 1815–1825, vol. 33(5).

*Primary Examiner*—Laura L. Stockton
(74) *Attorney, Agent, or Firm*—Robert C. Hall

(57) ABSTRACT

This invention relates to 8-aza prostanoid analogs which are generally $EP_4$ receptor agonists and are represented by Formula I:

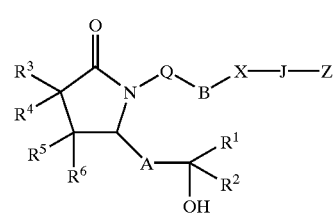

wherein Q, B, X, J, Z, A and $R^1$–$R^6$ are as defined, their synthesis and use for treatment of osteoporosis and increasing bone density.

35 Claims, No Drawings

2-PYRROLIDONE DERIVATIVES AS PROSTANOID AGONISTS

CROSS REFERENCE TO RELATED APPLICATION

This application claims benefit under Title 35 U.S.C. 119(e) of U.S. Provisional Application Ser. No. 60/305,762, filed Jul. 16, 2001, the disclosure of which is herein incorporated by reference.

FIELD OF THE INVENTION

This invention relates to certain 2-pyrrolidone derivatives, and associated pharmaceutical compositions, methods for use as selective prostaglandin $EP_4$ agonists, and methods of preparation thereof.

BACKGROUND OF THE INVENTION

There are many references in the literature to prostaglandins or prostanoids (PGs), a term which is generic to natural and synthetic prostaglandins and prostaglandin-like compounds, and it is well known that even slight differences in their chemical structures or stereochemical configurations will have profound effects on their biological activity.

Prostaglandins or prostanoids (PGs) are a group of bioactive compounds derived from membrane phospholipids, and are formed from 20-carbon essential fatty acids and contain a cyclopentane ring. They fall into several main classes designated by letters and are distinguished by substitutions to the cyclopentane ring. The main classes are further subdivided by subscripts 1, 2, or 3 which reflect their fatty acid precursors.

An example of a particular species of the prostaglandin E is $PGE_2$, with the following structure:

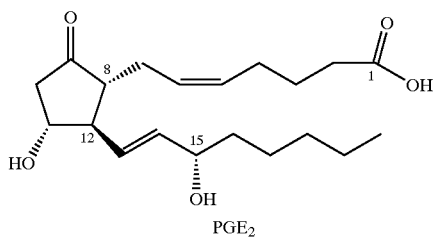

$PGE_2$

At present four different receptor subtypes of $PGE_2$ are known and they are designated $EP_1$, $EP_2$, $EP_3$, and $EP_4$.

Uses for compounds possessing a strong binding activity to $PGE_2$ receptors comprise the prevention and/or treatment of immunological diseases (autoimmune diseases, organ transplantation, etc.), asthma, abnormal bone formation, neuronal cell death, thrombosis and stroke, hepatopathy, abortion, male and female sexual dysfunction, premature birth, inflammation such as rheumatoid arthritis or retina neuropathy disorders such as glaucoma.

Prostaglandins and their associated receptors are more fully described in for example: M. Abramovitz et al., The Utilization of Recombinant Prostanoid Receptors to Determine the Affinities and Selectivities of Prostaglandins and Related Analogs, *Biochimica et Biophysica Acta* 2000, 1483, 285–293.

The involvement of prostaglandin E receptor agonists in bone resorption is described in, e.g., T. Suzawa et al., The Role of Prostaglandin E Receptor Subtypes in Bone Resorption: An Analysis Using Specific Agonists for the Respective EPs, *Endocrinology* 2000, 141, 1554–1559; K. Ono et al., Important Role of $EP_4$, a Subtype of Prostaglandin (PG) E Receptor, in Osteoclast-like Cell Formation from Mouse Bone Marrow Cells Induced by $PGE_2$, *J. of Endocrinology* 1998, 158, R1–R5; M. Suda et al., Prostaglandin E Receptor Subtypes in Mouse Osteoblastic Cell Line, *Endocrinology* 1996, 137, 1698–1705.

These selective prostaglandin E receptor agonists are also useful for the treatment of gastric lesions, see e.g. H. Araki, et al. The Roles of Prostaglandin E Receptor Subtypes in the Cytoprotective Action of Prostaglandin $E_2$ in Rat Stomach, *Aliment. Pharmacol. Ther.* 2000, 14 (Suppl. 1), 116–124; T. Kunikata, et al., E Type Prostaglandin Inhibits Indomethacin-Induced Small Intestinal Lesions Through $EP_3$ and $EP_4$ Receptors: A Study Using Rats and Knockout Mice, *Gastroenterology* 118, abstract #3787.

Other uses of prostaglandin E receptor agonists are for improvement of kidney function as described in, e.g., M. D. Breyer, et al, Prostaglandin E Receptors and the Kidney, *Am. J. Physiol.* 2000, 279, F12–F23, and K. E. Purdy, et al., $EP_1$ and $EP_4$ Receptors Mediate Prostaglandin $E_2$ Actions in the Microcirculation of Rat Kidney, *Am. J. Physiol.* 2000, 279, F755–F764; for thrombosis and stroke as well as for other conditions where an inhibition of platelet aggregation would be beneficial as described in, e.g., B. Z. S. Paul, et al, Distribution of Prostaglandin IP and EP Receptor Subtypes and Isoforms in Platelets and Human Umbilical Artery Smooth Muscle Cells, *Br. J. Haematol.* 1998, 102, 1204–1211; for antiinflammatory effects through inhibition of TNF-alpha generation as described in, e.g. K. K. Meja, et al. Characterization of prostanoid receptor(s) on human blood monocytes at which prostaglandin E2 inhibits lipopolysaccharide-induced tumor necrosis factor-alpha generation, *Br. J. Pharmacol.* 1997, 122, 149–157, and A. Eigler, et al. Anti-inflammatory activities of cAMP-elevating agents: enhancement of IL-10 synthesis and concurrent suppression of TNF production, *J. Leukoc. Biol.* 1998, 63, 101–107; or for glaucoma as described in, e.g., M. Takamatsu, et al. Localization of Prostaglandin E Receptor Subtypes in The Ciliary Body of Mouse Eye, *Exp. Eye Res.* 2000, 70, 623–628, and D. F. Woodward, et al, Molecular Characterization and Ocular Hypotensive Properties of the Prostanoid $EP_2$ Receptor, *J. Ocul. Pharmacol. Ther.* 1995, 11, 447.

Treatment of impotence and/or erectile dysfunction by using prostaglandins that are selective $EP_2$ and/or $EP_4$ receptor ligands have been disclosed in International Application Publication No. WO 99/02164 assigned to Pharmacia & Upjohn AB.

Additional information relating to prostaglandins and their receptors is described in *Goodman & Gillman's, The Pharmacological Basis of Therapeutics*, ninth edition, McGraw-Hill, New York, 1996, Chapter 26, pages 601–616.

8-Aza-11-deoxy-prostaglandin analogs corresponding to $PGE_2$ would have the following structure:

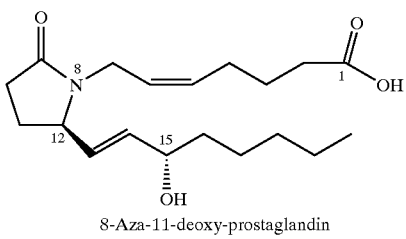

8-Aza-11-deoxy-prostaglandin

Substitution of a nitrogen for the carbon at C-8 causes a change in the three dimensional conformation of the resultant prostaglandin, and because structure is related to biological activity, such a conformational change will have a significant effect upon the biological activity. 8-Aza-11-deoxy prostaglandin E's with the natural side chains have been reported in the literature, see e.g. BE 841,165, assigned to Syntex USA, Inc.

Compounds of this invention are 8-azaprostaglandin analogs with a non-natural N-substituted side chain containing a heteroatom, which further changes the conformation of the resultant analogs. These compounds have high selectivity in their $EP_4$ receptor agonist activity. The increase in selectivity would alleviate the severe side effects frequently observed following administration of non-selective prostaglandins agonists. Therefore compounds of this invention are desirable.

SUMMARY OF THE INVENTION

This invention relates to compounds represented by Formula I:

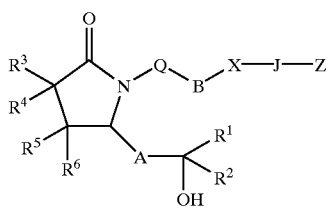

I wherein:
Q is —$CH_2$— or oxygen;
B is —$CH_2$—, —$(CH_2)_2$—, —$(CH_2)_3$—, —$(CH_2)_4$—, —$(CH_2)_5$—, —CH=CH—, —$CH_2$—CH=CH—, —CH=CH—$CH_2$—, or —$CH_2$—CH=CH—$CH_2$—, provided that when B is —CH=CH— or —CH=CH—$CH_2$—, then Q is —$CH_2$—,
X is —$NR^a$— (where $R^a$ is hydrogen, halogen, $(C_1-C_6)$alkyl or $(C_1-C_6)$acyl), —O—, —S—, —SO— or —$SO_2$— or a single bond, provided that when X is a single bond, then Q is oxygen;
J is —$(CR^bR^c)_n$— (where n is an integer from 1 to 4, and $R^b$ and $R^c$ are both hydrogen or one or two of $R^b$ and $R^c$ are lower alkyl and the remainder are hydrogen, or $R^b$ and $R^c$ if attached to the same carbon atom form a $C_2-C_5$-polymethylene group), or —$CH_2$—CH=CH—;
A is —$CH_2$—$CH_2$—, —CH=CH—, or —C≡C—;
Z is $CH_2OH$, —C(O)OR', —C(O)NR'R", —C(O)$NSO_2R'$, —P($C_1-C_6$)alkyl(O)(OR'), —PO(OR')$_2$, or tetrazol-5-yl; wherein R' and R" are independently from each other hydrogen or $(C_1-C_6)$alkyl;
n is 1, 2, 3 or 4;
$R^1$ is —$(CH_2)_pR^7$ or —$(CH_2)_qOR^8$, wherein $R^7$ and $R^8$ are each independently from each other $(C_1-C_6)$alkyl, halo $(C_1-C_6)$alkyl, $(C_3-C_8)$cycloalkyl, heterocyclyl, aryl or heteroaryl;

p and q are each independently from each other 0, 1, 2, 3, 4, or 5;
$R^2$ is hydrogen, $(C_1-C_6)$alkyl, $(C_1-C_6)$alkenyl, or $(C_1-C_6)$alkynyl; and
$R^3$, $R^4$, $R^5$ and $R^6$ are independently from each other hydrogen or $(C_1-C_6)$alkyl; or
a pharmaceutically acceptable salt or solvate, prodrug, single isomer or racemic or non-racemic mixture of isomers thereof.

In another aspect the invention relates to pharmaceutical compositions containing a therapeutically effective amount of at least one compound of Formula I or its pharmaceutically acceptable salt or solvate, prodrug, single isomer or racemic or non-racemic mixture of isomers in admixture with at least one suitable carrier, diluent or excipient.

In another aspect the invention provides a method of treatment of a disease, in particular a bone disease, in a mammal treatable by administration of a prostaglandin $EP_4$ receptor agonist, comprising administration of a therapeutically effective amount of a compound of Formula I or its pharmaceutically acceptable salt.

In another aspect the invention provides a process for preparing compounds of Formula I.

Definitions

Unless otherwise stated, the following terms used in the specification and claims have the meanings given below:

"Alkoxy" means a radical —OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" means a radical —SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently from each other with one or more substituents, preferably one, two, or three, selected from the group consisting of alkyl, haloalkyl, halo, nitro, cyano, amino, methylenedioxy, ethylenedioxy, Y-optionally substituted phenyl, Y-heteroaryl, Y-cycloalkyl, —Y-heterocyclyl, —Y—OR', —Y—NR'R", —Y—C(O)—R', —Y—S(O)$_{0-2}$—R'; —Y—N—$SO_2$—R', —Y—$SO_2$—NR'R", —Y—N—C(O)—NR'R", where Y is a bond or a $C_1-C_3$ alkylene group, and R' and R" are each independently from each other hydrogen, alkyl, haloalkyl, hydroxy, alkoxy, optionally substituted phenyl, heteroaryl, cycloalkyl, heterocyclyl. More specifically the term aryl includes, but is not limited to, phenyl, chlorophenyl, methoxyphenyl, methoxymethylphenyl, phenyloxyphenyl, 1-naphthyl, 2-naphthyl, and the derivatives thereof.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently from each other with one or more substituents, preferably one or two substituents, selected from alkyl, haloalkyl, halo, nitro, cyano, amino, methylenedioxy, Y-optionally substituted phenyl, Y-cycloalkyl, —Y-heterocyclyl, —Y—OR', —YNR'R", —Y—C(O)—R', —Y—O—C(O)—R', —Y—S(O)$_{0-2}$—R'; —Y—N—SO$_2$—R', —Y—SO$_2$—NR'R", —Y—N—C(O)—N—R'R", where Y is absent or a C$_1$–C$_3$ alkylene group and R' and R" are each independently from each other hydrogen, alkyl, haloalkyl, hydroxy, alkoxy, optionally substituted phenyl, cycloalkyl, heterocyclyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heterocyclyl" means a saturated or unsaturated non-aromatic cyclic radical of 3 to 8 ring atoms in which one or two ring atoms are heteroatoms selected from N, O, or S(O)$_{0-2}$, the remaining ring atoms being C, where one or two C atoms may optionally be replaced by a carbonyl group. The heterocyclyl ring may be optionally substituted independently from each other with one, two, or three substituents selected from alkyl, haloalkyl, halo, nitro, cyano, —Y-optionally substituted phenyl, Y-heteroaryl, Y-cycloalkyl, —Y—OR', —YNR'R", —Y—C(O)—R', —Y—S(O)$_{0-2}$—R'; —Y—N—SO$_2$—R', —Y—SO$_2$—NR'R", —Y—N—C(O)—N—R'R", where Y is absent or a C$_1$–C$_3$ alkylene group and R' and R" are each independently from each other hydrogen, alkyl, haloalkyl, hydroxy, alkoxy, optionally substituted phenyl, heteroaryl or cycloalkyl. More specifically the term heterocyclyl includes, but is not limited to, tetrahydropyranyl, piperidinyl, N-methylpiperidin-3-yl, piperazinyl, N-methylpyrrolidin-3-yl, 3-pyrrolidinyl, morpholinyl, thiomorpholinyl, thiomorpholino-1-oxide, thiomorpholino-1,1-dioxide, pyrrolinyl, imidazolinyl, N-methanesulfonyl-piperidin-4-yl, and the derivatives thereof.

"Leaving group" has the meaning conventionally associated with it in synthetic organic chemistry, i.e., an atom or a group capable of being displaced by a nucleophile and includes halo (such as chloro, bromo, and iodo), alkylsulfonyloxy, arylsulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently from each other with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy and acyl.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J., Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

The compounds of this invention may exist in stereoisomeric form, therefore they can be produced as individual stereoisomers or as mixtures.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:
(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1–92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. M. Futs, *Protective Groups in Organic Chemistry*, (Wiley, 3$^{rd}$ ed. 1999) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Prostaglandin analog" is a non-naturally-occurring compound which is structurally similar to a prostaglandin.

"Prostaglandin receptor" or "prostanoid receptor" is a naturally-occurring protein that binds prostaglandins, which when bound alters the function of a cell. Prostaglandin receptors may be characterized as either excitatory or relaxant. Such receptors include but are not limited to $EP_1$, $EP_2$, $EP_3$, $EP_4$, DP, FP, IP, $TP_1$, and $TP_2$. These receptors are further discussed by Coleman et al, in *Pharmacological Reviews*, 1994, Volume 6, No. 2, pages 205–229.

Nomenclature

The naming and numbering of the compounds of this invention is illustrated below:

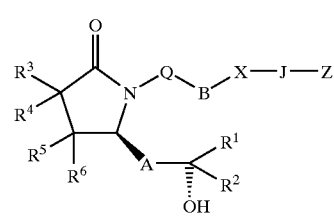

I

In general, the nomenclature used in this Application is based on AUTONOM™ v.4.0 a Beilstein Institute computerized system for the generation of IUPAC systematic nomenclature.

For example, a compound of Formula I wherein Q is —$CH_2$—; B is —($CH_2$)—; X is —S—; J is —($CH_2$)$_3$—; Z is —COOH; $R^2$, $R^3$, $R^4$, $R^5$ and $R^6$ are hydrogen; A is —CH═CH—; and $R^1$ is n-pentyl is named 4-[(2-{(2R)-2-[(1E,3S)-3-hydroxyoct-1-enyl]-5-oxopyrrolidin-1-yl}ethyl)thio]-butanoic acid.

Preferred Embodiments

While the broadest definition of this invention is set forth in the Summary of the Invention, certain compounds of Formula I are preferred.

Compounds where Z is —C(O)OR', $CH_2OH$ or tetrazol-5-yl are preferred with Z being COOH being particularly preferred.

Compounds where Q and B together form —($CH_2$)$_n$ where n is an integer from 2 to 5 are preferred with n being 2 or 3 being particularly preferred.

Compounds where X is —O— or —S— are preferred.

Compounds where J is —(CH$_2$)$_3$—; —(CHR$^a$)$_3$ where one of R$_a$ is lower alkyl; or —CH$_2$—CH=CH— are preferred.

Compounds where A is —CH$_2$—CH$_2$— or CH=CH are preferred.

Compounds where R$^2$, R$^3$, R$^4$, R$^5$ and R$^6$ are hydrogen are preferred.

Compounds where R$^7$ is aryl or heteroaryl are preferred with R$^7$ being phenyl optionally substituted with of alkyl, trifluoromethyl, halo, —Y—R$^9$ or —Y—OR$^9$, wherein Y is a bond and R$^9$ is (C$_1$–C$_6$)alkyl, halo or optionally substituted phenyl being particularly preferred.

In a first embodiment Q, B, X, J, Z, A, R$^2$, R$^3$, R$^4$, R$^5$ and R$^6$ are as defined in the Summary of the Invention, R$^1$ is —(CH$_2$)$_p$R$^7$, and R$^7$ is alkyl or (C$_3$–C$_8$)cycloalkyl. Preferably R$^7$ is methyl and p is 4.

In a second embodiment, Q, B, X, J, Z, A, R$^2$, R$^3$, R$^4$, R$^5$ and R$^6$ are as defined in the Summary of the Invention and R$^1$ is —(CH$_2$)$_p$R$^7$ wherein R$^7$ is aryl, heteroaryl or heterocyclyl. Preferably, R$^7$ is an optionally substituted phenyl wherein at least one substituent is selected from (C$_1$–C$_6$) alkyl, trifluoromethyl, halo, —Y—R$^9$, —Y—OR$^9$, and —Y—C(O)R$^9$, wherein Y is a bond or a (C$_1$–C$_3$)alkylene group, and R$^9$ is (C$_1$–C$_6$)alkyl, aryl, heteroaryl, or heterocyclyl. More preferably, R$^7$ is aryl or heteroaryl, and p is 0. Still more preferably, R$^7$ is aryl or heteroaryl, and p is 1.

In a third embodiment, R$^1$, R$^2$, R$^3$, R$^4$, R$^5$, R$^6$ A, J and Z are as defined in the Summary of the Invention, and Q-B together are —(CH$_2$)$_{2-6}$ and X is —NH—, —O— or —S—. Preferably, Q-B together are —CH$_2$—CH$_2$—. More preferably, within this embodiment, R$^1$ is —(CH$_2$)$_p$R$^7$ wherein R$^7$ is aryl or heteroaryl.

In a fourth embodiment, R$^1$, R$^2$, R$^3$, R$^4$, R$^5$, R$^6$ A, B, J and Z are as defined in the Summary of the Invention, and Q is oxygen.

In a fifth embodiment, R$^1$, R$^2$, R$^3$, R$^4$, R$^5$, R$^6$ A, Q, B, X and Z are as defined in the Summary of the Invention and J is —(CH$_2$)$_3$— or —(CHR$^a$)$_3$ where one of R$_a$ is lower alkyl.

Representative compounds of formula I are:

4-[(2-{(2R)-2-[(1E,3S)-3-hydroxy-oct-1-enyl]-5-oxo-pyrrolidin-1-yl}ethyl)thio]butanoic acid, {4-[2[R-(3-hydroxy-oct-1E-enyl)5-oxo-pyrrolidin-1-yl] butylsulfanyl}acetic acid, {4-[2[R-(1E-3S-3-hydroxy-oct-1-enyl)5-oxo-pyrrolidin-1-yl]butylsulfanyl}acetic acid {4-[(R)-2-((E)-3-hydroxy-oct-1-enyl)-5-oxo-pyrrolidin-1-yl]-butoxy}acetic acid, (4-{(R)-2-[(E)-3-Hydroxy-3-(5-trifluoromethyl-furan-2-yl)-propenyl]-5-oxo-pyrrolidin-1-yl}-butylsulfanyl)acetic acid, 4-{2-[(R)-2-((S)-(E)-3-hydroxy-oct-1-enyl)-5-oxo-pyrrolidin-1-yl]-ethanesulfinyl}-butyric acid, 4-{2-[(R)-2-((S)-(E)-3-hydroxy-oct-1-enyl)-5-oxo-pyrrolidin-1-yl]-ethanesulfonyl}-butyric acid, {(Z)-4-[(R)-2-((E)-3-hydroxy-oct-1-enyl)-5-oxo-pyrrolidin-1-yl]-but-2-enyloxy}acetic acid, {4-[(R)-2-((E)-(S)-3-Hydroxy-oct-1-enyl)-5-oxo-pyrrolidin-1-yl]-butoxy}-acetic acid, (4-{(R)-2-[(S)-(E)-3-hydroxy-4-(3-trifluoromethyl-phenyl)-but-1-enyl]-5-oxo-pyrrolidin-1-yl}-butoxy)-acetic acid, (4-{(R)-2-[(E)-3-hydroxy-3-(2'-methyl-biphenyl-3-yl)-propenyl]-5-oxo-pyrrolidin-1-yl}-butoxy)-acetic acid, (4-{(R)-2-[(E)-3-(4'-chloro-biphenyl-3-yl)-3-hydroxy-propenyl]-5-oxo-pyrrolidin-1-yl}-butoxy)-acetic acid, 4-{2-[(R)-2-((E)-3-hydroxy-3-pentyl-oct-1-enyl)-5-oxo-pyrrolidin-1-yl]-ethylsulfanyl}-butyric acid, 4-{2-[(R)-2-((E)-3-hydroxy-3-methyl-oct-1-enyl)-5-oxo-pyrrolidin-1-yl]-ethylsulfanyl}-butyric acid, 4-[2-((S)-2-{(R)-3-[3-(3-Fluoro-phenoxy)-phenyl]-3-hydroxy-propyl}-5-oxo-pyrrolidin-1-yl)-ethylsulfanyl]-butyric acid, 4-{2-[(R)-2-((S)-(E)-3-hydroxy-oct-1-enyl)-5-oxo-pyrrolidin-1-yl]-ethylsulfanyl}-3-methyl-butyric acid, 4-{2-[(R)-2-((S)-(E)-3-hydroxy-oct-1-enyl)-5-oxo-pyrrolidin-1-yl]-ethylsulfanyl}-2-methyl-butyric acid, 4-{2-[(R)-2-((S)-(E)-3-hydroxy-oct-1-enyl)-5-oxo-pyrrolidin-1-yl]-ethylsulfanyl}-4-methyl-butyric acid, (1-{2-[(R)-2-((S)-(E)-3-hydroxy-oct-1-enyl)-5-oxo-pyrrolidin-1-yl]-ethylsulfanylmethyl}-cyclopropyl)-acetic acid, 5-{2-[(R)-2-((S)-(E)-3-hydroxy-oct-1-enyl)-5-oxo-pyrrolidin-1-yl]-ethylsulfanyl}-acetic acid, 3-{2-[(R)-2-((S)-(E)-3-hydroxy-oct-1-enyl)-5-oxo-pyrrolidin-1-yl]-ethylsulfanyl}-propionic acid, 5-{2-[(R)-2-((S)-(E)-3-hydroxy-oct-1-enyl)-5-oxo-pyrrolidin-1-yl]-ethylsulfanyl}-pentanoic acid, 4-{2-[(R)-2-((S)-(E)-3-hydroxy-oct-1-enyl)-5-oxo-pyrrolidin-1-yl]-ethylsulfanyl}-2-butenyruic acid, 4-[2-((S)-2-{(R)-3-[3-(4'-chloro-2'-methylphenyl)-phenyl]-3-hydroxy-propyl}-5-oxo-pyrrolidin-1-yl)-ethylsulfanyl]-butyric acid, 4-[2-((S)-2-{(S)-3-[3-(4'-chloro-2-methylphenyl)-phenyl]-3-hydroxy-propyl}-5-oxo-pyrrolidin-1-yl)-ethylsulfanyl]-butyric acid, 4-[2-((S)-2-{(R)-3-[3-(2',4'-difluorophenyl)-phenyl]-3-hydroxy-propyl}-5-oxo-pyrrolidin-1-yl)-ethylsulfanyl]-butyric acid, 4-[2-((S)-2-{(R)-3-[3-(4'-methoxy-2'-methyl)-phenyl]-3-hydroxy-propyl}-5-oxo-pyrrolidin-1-yl)-ethylsulfanyl]-butyric acid, 6-[2-((S)-(E)-3-Hydroxy-oct-1-enyl)-5-oxo-pyrrolidin-1-yloxy]-hexanoic acid, and 3-{3-[2-(3-Hydroxy-oct-1-ynyl)-5-oxo-pyrrolidin-1-yl]-propylsulfanyl}-propionic acid.

The structure of the compounds of Formula I may include optical isomers, diastereomers, or enantiomers of the above structure or pharmaceutically-acceptable salts, biohydrolyzable amides, esters, or imides thereof. Preferred stereochemistry mimics that of naturally occurring PGE$_2$.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming pharmaceutically acceptable base addition salts. All of these forms are within the scope of the present invention.

General Synthetic Scheme

Compounds of this invention can be made by the methods depicted in the reaction schemes shown below. One of skill in the art will understand that certain modifications to the schemes are within the scope of the present invention as, for example, certain steps involving the use of protecting groups for functional groups that are not compatible with particular reaction conditions.

The starting materials and reagents used in preparing these compounds are either available from commercial suppliers or are prepared by methods known to those skilled in the art. These schemes are merely illustrative of some methods by which the compounds of this invention can be synthesized, and various modifications to these schemes can be made and will be suggested to one skilled in the art having referred to this disclosure.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Scheme A

Scheme A outlines methods to prepare compounds of general formula I when Q is —CH$_2$—.

Compounds of formula a (Scheme A) are known in the art. For example (R)-5-(hydroxymethyl)-2-pyrrolidinone, wherein $R^3$, $R^4$, $R^5$ and $R^6$ are hydrogen, is a commercial product and its preparation is described in S. Saijo et al. *Chem. Pharm. Bull.* 1980, 28, 1449–1458; (R)-3,3-dimethyl-5-(hydroxymethyl)-2-pyrrolidinone, wherein $R^3$ and $R^4$ are methyl and $R^5$ and $R^6$ are hydrogen, can be prepared according to Y. Nakagawa, et al., *Tetrahedron* 1998, 54, 10295–10307; and 4,4-dimethyl-5-(hydroxymethyl)-2-pyrrolidinone, wherein $R^3$ and $R^4$ are hydrogen and $R^5$ and $R^6$ are methyl can be prepared according to R. L. Mackman, et al., *J. Chem. Soc., Perkin Trans.,* 1997, 2111–2122.

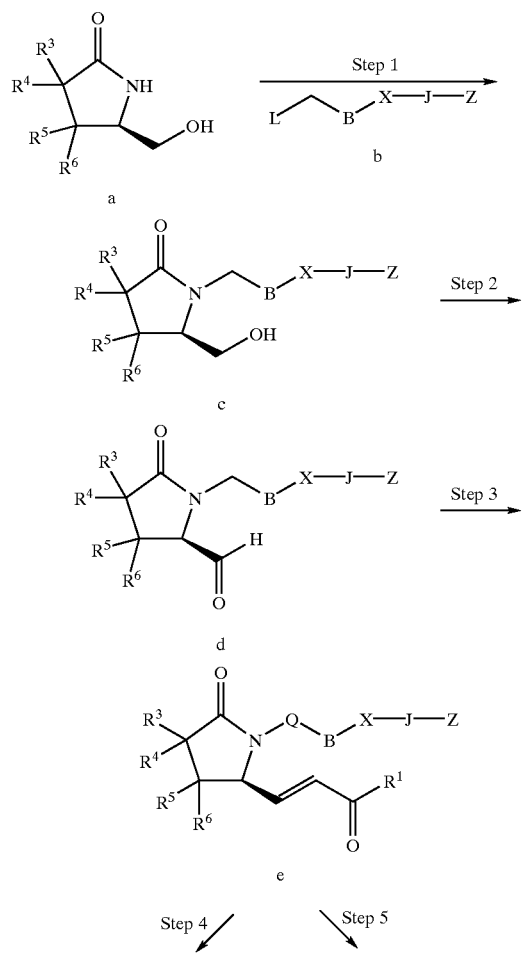

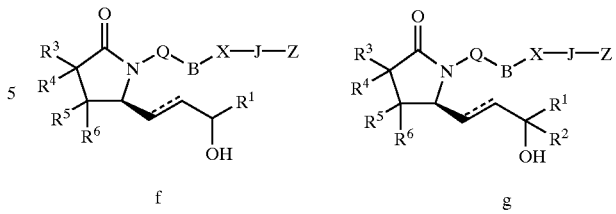

As an initial step, the hydroxyl group in compound a is protected by methods known in the art and described herein above. Methods of protecting the hydroxyl in a as acetals have been described by S. Saijo et al. *Chem. Pharm. Bull.* 1980, 28, 1449–1458. Alternative protective groups are silyl ethers. A silyl ether can be prepared with any halotrialkylsilane such as for example chlorotriisopropylsilane, chlorodimethylphenylsilane, or t-butylchlorodimethyl silane, in an inert organic solvent such as, but not limited to, dichloromethane, tetrahydrofuran, or N,N-dimethylformamide with a weak base such as imidazole, triethylamine, or pyridine.

The O-protected 5-hydroxymethyl-2-pyrrolidinone is dissolved in a polar solvent such as tetrahydrofuran, N-methyl-2-pyrrolidinone, or N,N-dimethylformamide, and treated with a base such as sodium hydride, potassium hexamethyldisilazide, or potassium tert-butoxide to produce an anion, and reacted with an alkyl derivative of general formula b, wherein L is a leaving group, preferably a halogen, and Z is an ester group as defined above. Deprotection of the protected hydroxy group in an alcoholic solvent such as methanol, ethanol or 2-propanol and a catalytic amount of an acid such as trifluoroacetic acid, para-toluene sulfonic acid, or hydrochloric acid yields a compound c.

Compound c is oxidized with an oxidizing reagent that will arrest transformation at the aldehyde to yield an aldehyde of general structure d. The oxidizing agents that can be used are, for example, dimethylsulfoxide-trifluoroacetic anhydride then triethylamine sequence, sodium hypochlorite with catalytic 2,2,6,6-tetramethyl-1-piperidinyloxy radical, 1,1,1-triacetoxy-1,1-dihydro-1,2-benziodoxol-3(1H)-one, N-methyl morpholine-N-oxide with catalytic tetrapropylammonium perruthenate, or pyridinium chlorochromate in the presence of an inert support such as Celite™, in an inert organic solvent such as 1,2-dichloroethane, dichloromethane or benzene.

Reaction of compound d with a β-ketophosphonate, of general formula $R^1$—C(O)—CH$_2$PO(OCH$_3$)$_2$ (k, see Scheme C for their preparation) in the presence of a base such as, for example, sodium hydride, potassium t-butoxide, potassium hexamethyldisilazide, or lithium chloride with a tertiary amine, in an inert ethereal solvent such as tetrahydrofuran, 1,2-dimethoxyethane, or t-butylmethylether, yields ketone of general formula e.

In step 4, reduction of ketone e with a hydride, for example sodium borohydride in a solvent such as dichloromethane, toluene, ethanol, or tetrahydrofuran yields a diasteromeric mixture of alcohols of formula f wherein $R^2$ is hydrogen. If the preferential formation of one of the diastereomer is desired such as the S-hydroxyl isomer when $R^1$ is normal alkyl, the stoichiometric combination of lithium aluminum hydride-ethanol-(S)-(−)-binaphthol as described by R. Noyori, et al. *J. Am. Chem. Soc.* 1984, 106, 6717–6725 can be used; or if the R-hydroxyl isomer is desired, the combination of catalytic amounts of (R)-2-methyl-"CBS"-oxazaborolidine with stoichiometric borane-dimethyl sulfide as described by E. J. Corey, et al., *J. Am. Chem. Soc.* 1987, 109, 7925–7926; or stoichiometric amounts of (R)-3-pinanyl-9-borabicyclo[3.3.1]nonane as described by M. M. Midland et al., *J. Am. Chem. Soc.* 1980, 102, 867–869 is used. Catalytic hydrogenation of the double bond with Raney Ni or Pd on carbon yields a compound of general formula f, wherein the side chain is saturated.

Alternatively, reaction of compound e in Step 5 with a metal or a magnesium halide of general formula $R^2M$, more preferably a Grignard reagent of general formula $R^2MgBr$, wherein M is a metal and $R^2$ is as defined above, yields compound g If the compound with a saturated side chain is desired, the double bond can be reduced by the method described above.

The ester group Z is hydrolyzed, if desired, to the —C(O)OH by hydrolysis using the procedures well known by a person of ordinary skill in the art, for example, addition of a base such as lithium, sodium of potassium hydroxide, or an acid such as sulfuric acid or hydrochloric acid in a protic or ethereal solvent containing water, or by employing a Lipase type VII in 0.05 M aqueous phosphate buffer at pH 6.8 as described by C. Luthy, et al. *J. Am. Chem. Soc.* 1978, 100, 6211–6217.

Alkyl derivatives b for preparing compounds where Z is other than C(O)OR' may be prepared by the procedures known in the art. For example, an alkyl derivative of formula b can be reacted and subsequently converted to Z as a tetrazol-5-yl as described by W. S. Marshall, et al. *J. Med Chem.* 1987, 30, 682–689.

Scheme B

Scheme B describes a general method for preparing compounds of formula I wherein Q is —$CH_2$— and B is —$CH_2$— wherein $R^1$ is aryl and $R^2$ is H.

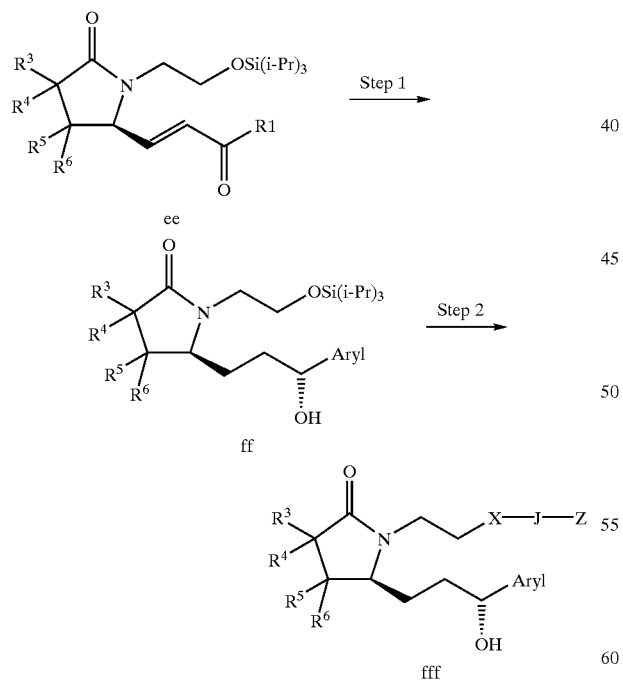

Compounds of formula ee are prepared according to Scheme A by the use of an alkyl halide, such as β-bromo ethanol trialkylsilyl ether, in the N-alkylation step and the use of β-ketophosphonate of the compound k in the olefination step. Compounds of general formula ff are prepared by initial reduction of the double bond in compound ee by treatment with a hydride source, such as $[CuH(Ph_3P)]_6$ or lithium or potassium (sec-butyl)$_3$borohydride, or by exposure to hydrogen gas with a metal surface present, such as platinum oxide or palladium on carbon. Diastereomeric alcohols of the general formula ff are produced with a hydride, for example sodium borohydride in a solvent such as dichloromethane, toluene, ethanol, or tetrahydrofuran. If the preferential formation of one of the 15-diastereomers is desired, as for example, if it is desired to prepare the R-hydroxyl isomer when $R^1$ is aryl; the stoichiometric combination of lithium aluminum hydride-ethanol-(R)-(−)-binaphthol as described by R. Noyori, et al. *J. Am. Chem. Soc.* 1984, 106, 6717–6725 is used. If however, it is desired to prepare the S-hydroxyl isomer, the combination of catalytic amounts of (S)-2-methyl-"CBS"-oxazaborolidine with stoichiometric borane-dimethyl sulfide as described by E. J. Corey, et al., *J. Am. Chem. Soc.* 1987, 109, 7925–7926; or stoichiometric amounts of (S)-3-pinanyl-9-borabicyclo[3.3.1]nonane as described by M. M. Midland et al., *J. Am. Chem. Soc.* 1980, 102, 867–869 is used.

Deprotection of the hydroxyl group in compound ff by standard conditions cited earlier such as sodium hydroxide in aqueous methanol or tetrabutylammonium fluoride in tetrahydrofuran. The resultant diol can be selectively derivatized at the primary hydroxyl group with benzenesulfonyl chloride or methanesulfonyl chloride in the presence of a trialkylamine, such as triethylamine at −25 to 0° C. to obtain the corresponding monosulfonate.

The above monosulfonate is then reacted with the nucleophile lithium or potassium-X-J-Z, such as the potassium thiolate generated by the treatment of potassium methoxide with γ-thiobutyrolactone, in an inert ethereal solvent such as tetrahydrofuran or 1,2-dimethoxyethane to produce compound fff wherein X is S. The ester group Z is hydrolyzed, if desired, to the —C(O)OH by hydrolysis using the procedures described earlier.

Scheme C

Scheme C describes a general method of preparing a phosphonate of formula k in turn used in Scheme A above to introduce the lower side-chain wherein $R^1$ is aryl.

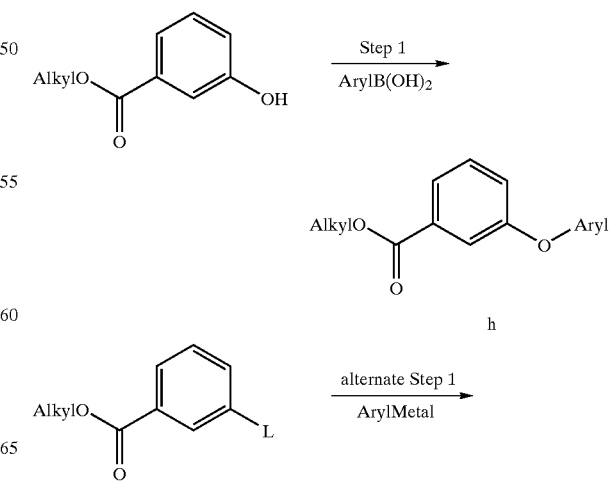

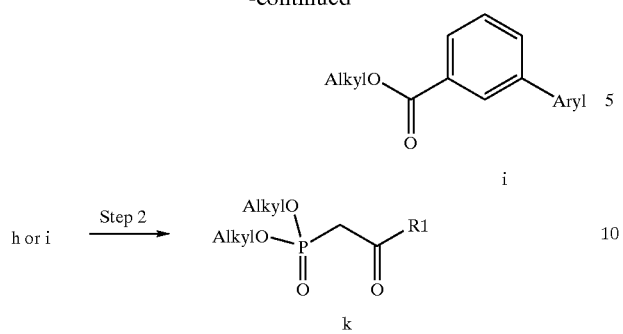

The benzoic acid derivatives, as starting materials, where L is a leaving group as defined earlier, are either commercially available or synthesized by those of ordinary skill in the art and are converted to compounds of formula h and j, respectively. The conditions for the preparation of compounds of formula h are described in D. A. Evans et al. *Tetrahedron Lett.* 1998, 39, 2937. The methods for the preparation of compounds of formula k are described in A. M. Echavarren and J. K. Stille *J. Am. Chem. Soc.* 1987, 109, 5478–5486, N. Miyaura and A. Suzuki *Chem. Rev.* 1995, 95, 2457–2483, and A. F. Littke et al. *J. Am. Chem. Soc.* 2000, 122, 4020–4028. Compounds h and j are converted into compound k by exposure to a dialkyl methyl phosphonate, which is initially treated with a base such as normal butyllithium or lithium diisopropylamide in an inert ether solvent such as tetrahydrofuran, or t-butylmethyl ether.

Scheme D

Scheme D describes a general method of preparing compounds of formula I wherein Q is —O— and X is a bond.

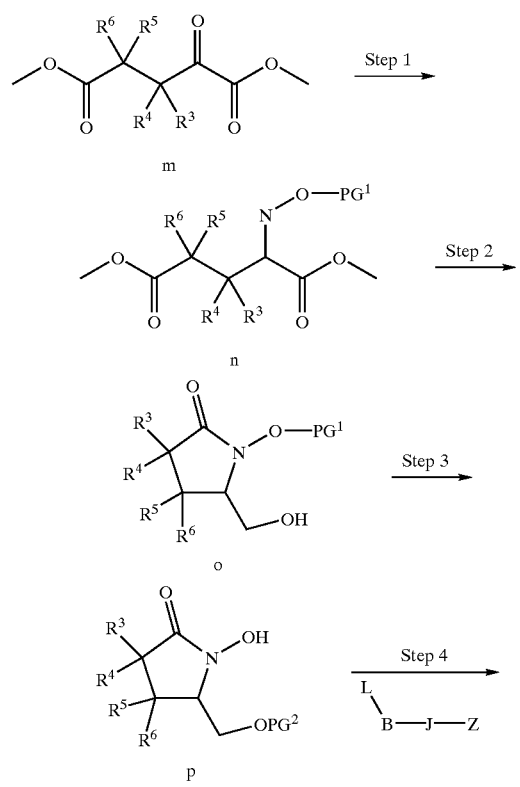

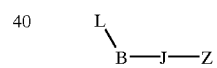

The starting compounds of formula m are known in the art. For example, dimethyl 2-oxoglutarate, wherein $R^3$, $R^4$, $R^5$ and $R^6$ are hydrogen, is a commercial product. Sequential treatment of m with a hydroxyamine, for example O-benzylhydroxylamine, in the presence of a mild base such as pyridine or sodium acetate then exposure to a reducing agent such as borane-pyridine complex or sodium triacetoxyborohydride yields compound n wherein protective group$^1$ (PG$^1$) is benzyl. Treatment of compound n with a base such as iso-propylmagnesium bromide or potassium tert-butoxide, followed by treatment with a reducing agent, such as sodium borohydride converts the pendent ester to produce lactam o. In step 3, the resultant hydroxyl of compound o is first protected, appropriately such that PG$^1$ can be removed in the presence of PG$^2$. The lactam p is produced, when for example PG$^1$ is benzyl and PG2 is t-butyldimethylsilyl, using a catalyst such as palladium on carbon or platinum oxide and hydrogen gas.

The N-hydroxyl lactam p is dissolved in a polar solvent such as tetrahydrofuran, N-methyl-2-pyrrolidinone, or N,N-dimethylformamide, and treated with a base such as sodium hydride, potassium hexamethyldisilazide, or potassium tert-butoxide to produce an anion, that can then be reacted with an alkyl derivative of formula:

$$L\diagdown_{B-J-Z}$$

wherein L is a leaving group, preferably a halogen, followed by deprotection, for example, with potassium or tetrabutylammonium fluoride to furnish compounds of the general formula cc. The compounds of formula cc are converted into compounds of the general formula g according to the method described in Scheme A above.

Scheme E

Scheme E describes a method of preparing a compound of formula I wherein A is a carbon to carbon triple bond.

Scheme E

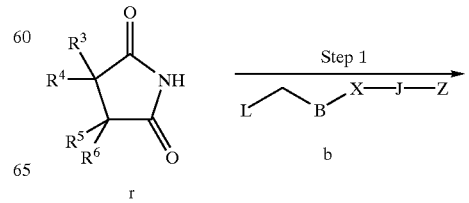

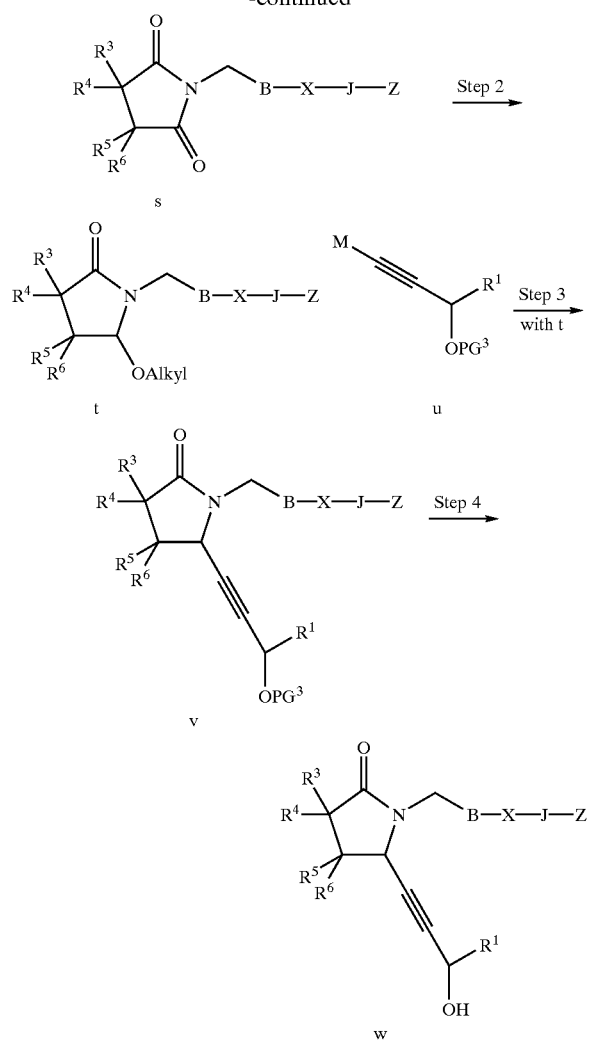

In general, the alkylation of r with an alkyl halide of general formula b, wherein L, B and Z are as defined previously and Q is —CH$_2$—, in a polar aprotic solvent such as N-methyl-2-pyrrolidinone, N,N-dimethylformamide, tetrahydrofuran, or acetonitrile in the presence of a weak base such as sodium methoxide, potassium carbonate, or potassium t-butoxide produces a cyclic imide of formula s. Alkoxy-lactams of general formula t are prepared by the reduction of compound s with lithium or sodium borohydride in an alcoholic solvent, and in the presence of an acid such as citric acid, trifluoroacetic acid, hydrochloric acid, or hydrobromic acid, as described by J. C. Hubert, et al., *Tetrahedron* 1975, 31, 1437–1441.

The reaction of compound t with an organotinalkynyl derivative reagent of general formula u, wherein PG$^3$ is a protective group such as for example a silyl ether, and M is a metal, typically in the presence of a Lewis Acid such as a magnesium halide, boron trihalide, titanium (IV) salt, or tin (IV) salt, followed by deprotection affords compound w.

Compound w wherein Z is —C(O)OH can be prepared from the esters by hydrolysis as described in Scheme A.

Utility

The compounds of the present invention are selective EP$_4$ prostaglandin agonists and may be used to treat several disease states associated with prostaglandin EP$_4$ receptor-mediated diseases, particularly for disease states associated with bone disorders, characterized by low bone mass and deterioration of bone tissue, with a consequent increase in bone fragility and susceptibility in fracture, especially those that require a significant increase in bone mass, bone volume, or bone strength. Conditions associated with low bone mass refer to a condition where the level of bone mass is below the age specific normal. Childhood idiopathic and primary osteoporosis are also included. Included in the treatment of osteoporosis is the prevention or attenuation of long term complications such as curvature of the spine, loss of height, prosthetic surgery, fracture healing, and prevention of prostate malfunctioning. Those skilled in the art will recognize that the term bone mass actually refers to bone mass per unit area which is sometimes referred to as bone mineral density. It has been discovered that the 8-aza-11-deoxy prostaglandin analogs of the present invention are useful for treating bone disorders.

Other uses of these compounds include prevention and/or treatment of allergy, alveolar abscess, Alzheimer's disease, Amyotrophic lateral sclerosis (ALS), arthritis, asthma, atopy, bronchitis, burns, cancer, cardiovascular disease, Crohn's disease, chronic obstructive respiratory diseases, congestive heart failure, gingivitis, glomerulonephritis, hepatitis, hepatic injury, acute hepatitis, hypertension, hypercytokinemia, immune disorders, inflammatory bowel disease, Kawasaki disease, liver failure, liver disease, lung failure, macrophage activation syndrome, multiorgan failure, multiple sclerosis, myocardial ischemia, nephritis, neurodegeneration, neuronal death, organ transplant rejection, periodontitis, platelet aggregation, pulmonary injury, pulmonay fibrosis, pulmonary emphysema, renal failure, renal insufficiency, renal disorders, respiratory diease, septicemia, sepsis, shock, sleep and platelet aggregation disorders, Still disease, systemic granuloma, thrombosis, ulcerative colitis and uremia or as osteogenesis promotor.

Testing

The compounds of Formula I bind and act on EP$_4$ receptors which is a subtype of PGE$_2$ receptor. The effects of the compounds of the present invention may be measured with the binding assay using cells expressing prostanoid receptor subtypes as described in more detail in Example 10. The competitive binding activity of these compounds to the intended target may be measured as described in Example 11. The compounds of this invention may be evaluated for their effect on bone mass density in accord with the procedures of Gunness-Hey and Hock, *Metab. Bone Dis.* 5, 177–181 (1984), as described in more detail in Example 12.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.0005–10 mg per kilogram body weight of the recipient per day; preferably about 0.001–1 mg/kg/day. Thus, for administration to a 70 kg person, the dosage range would preferably be about 0.1 mg to 70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula I based on the total formulation, with the balance being one or more suitable pharmaceutical excipients. Preferably, the compound is present at a level of about 1–80 wt %. Representative pharmaceutical formulations containing a compound of Formula I are described in Example 8.

EXAMPLES

The following preparations and examples are given to enable those skilled in the art to more clearly understand and to practice the present invention. They should not be considered as limiting the scope of the invention, but merely as being illustrative and representative thereof.

Preparation 1

[(4-Chlorobutyl)thio]acetic Acid Methyl Ester

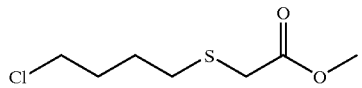

A solution of methyl thioglycolate (10.0 mL, 113 mmol) in tetrahydrofuran (200 mL) at −78° C. under argon atmosphere was treated dropwise with n-butyllithium (2.5 M hexanes solution, 45 mL, 113 mmol). After 1 h at −78° C., the cloudy solution was rapidly treated with 1-bromo-4-chlorobutane (13.0 mL, 113 mmol) and allowed to warm to room temperature overnight. It was poured into water and hexanes, washed with cold aqueous sodium hydroxide solution (0.1 M) followed with saturated aqueous ammonium chloride, and the organic layer was stored over anhydrous sodium sulfate. The volatiles were removed and the residue was purified by chromatography and eluted with 8:1 hexane:ethyl acetate to yield [(4-chlorobutyl)thio]acetic acid methyl ester (10.7 g, 54.5 mmol) as a colorless liquid: EIMS m/z 198 ($M^+$ with $^{37}Cl$), 196 ($M^+$ with $^{35}Cl$).

Preparation 2

Methyl 4-[(2-chloroethyl)thio]butanoate

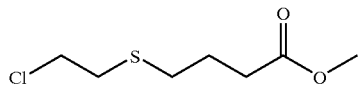

A 0° C. isopropanol (70 mL) solution of 4-mercaptobutyric acid (3.85 g, 20 mmol) was treated with sodium hydride in four portions (95%, 1.56 g total, 65 mmol) over 20 minutes and allowed to warm to room temperature. 1-Bromo-2-chloroethane (11 mL, 128 mmol) was added rapidly with the resulting suspension stirred vigorously for 2 days, then the volatiles were removed, and the residue was partitioned between 5% aqueous acetic acid and ethyl acetate. The combined organic extracts were washed with brine and stored over sodium sulfate. The extract was filtered and the volatiles were removed under vacuum. The residue was dissolved in methanol (60 mL) and cooled to 0° C. under argon atmosphere. Thionyl chloride (5 mL, 69 mmol) was added dropwise and the solution was stirred at room temperature. After 2-3 hours, the volatiles were removed, toluene was added, and the volatiles were removed again. Chromatography yielded (2.93 g, 14 mmol) of methyl 4-[(2-chloroethyl)thio]butanoate as a colorless oil: MS ($NH_3$) m/z 199 ($M+1^+$ with $^{37}Cl$), 197 ($M+1^+$ with $^{35}Cl$).

Preparation 3

Z-4-Chloro-but-2-enyloxy)-acetic Acid Ethyl Ester

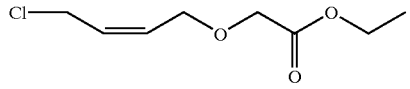

To a solution of sodium hydride (1.17 g, 48 mmol) in 50 mL DMF at 0° C. under nitrogen was added ethyl glycolate (4.5 mL, 48 mmol), and the reaction was stirred for 1 hr. Z-1,4-dichloro-2-butene (7.6 mL, 72 mmol) was quickly added, and the reaction was allowed to come to room temperature and stirred overnight. After pouring into water, the mixture was extracted with diethyl ether, dried and concentrated. The resulting of product was purified with choromatography to afford 2.7 g of Z-4-chloro-but-2-enyloxy)-acetic acid ethyl ester as a crude oil.

Preparation 4

(4-Bromo-butoxy)-acetic Acid Ethyl Ester

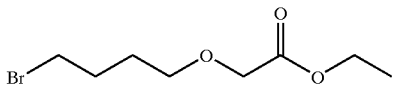

To a solution of sodium hydride in 40 mL DMF stirred at 0° C. was slowly added ethyl glycolate (5 g, 48 mmol). After 1 hour, 1,4-dibromobutane (8.6 mL, 72 mmol) was added, and the mixture was stirred for an additional 2 hours. The reaction was allowed to warm to room temperature for an additional 3 hours. A sodium bicarbonate solution was added, and the organic layer was dried over anhydrous sodium sulfate, concentrated and the residue was purified by chromatography to afford a colorless oil.

Example 1

4-[(2-{(2R)2-[(1E,3S)-3-hydroxyoct-1-enyl]-5-oxopyrrolidin-1-yl }ethyl)thio]butanoic Acid (1)

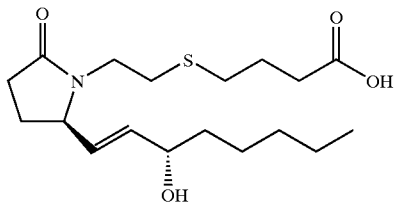

Step 1
Methyl 4-({2-[(5R)-5-(hydroxymethyl)-2-oxo pyrrolidin-1-yl]ethyl}thio)butanoate

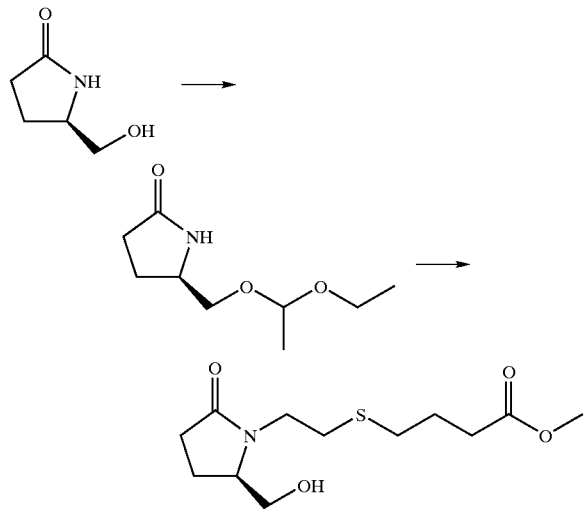

To a solution of (5R)-5-(hydroxymethyl)pyrrolidin-2-one (Aldrich, 8.86 g, 77 mmol) in 70 mL of chloroform at room temperature under an argon atmosphere was added ethyl vinyl ether (10.4 mL, 108 mmol) and catalytic anhydrous trifluoroacetic acid (0.2 mL). After stirring for 3 hours, the reaction was partitioned between methylene chloride (150 mL) and aqueous sodium bicarbonate solution (150 mL) and the phases were separated. The organic phase was dried (K$_2$CO$_3$) and filtered. The filtrate was evaporated under reduced pressure to give 14.7 g of the (5R)-5-(1-ethoxyethoxymethyl)pyrrolidin-2-one.

To a solution of (5R)-5-(1-ethoxyethoxymethyl) pyrrolidin-2-one (3.31 g, 17.7 mmol) in 50 mL of anhydrous dimethylformamide at 0° C. under an argon atmosphere was added potassium iodide (3.22 g, 19.4 mmol) and sodium hydride (95%, 0.44 g, 17.7 mmol). The cooling bath was removed and the reaction was stirred for 30 minutes. A solution of methyl 4-[(2-chloroethyl)thio]butanoate (3.46 g, 17.7 mmol) in 5 mL anhydrous dimethylformamide was added and the reaction solution was warmed to 50° C. and stirred for 40 hours. The volatiles were removed via simple distillation under vacuum. Ethyl acetate (150 mL) and aqueous ammonium chloride solution (50 mL) were then added to the crude residue. Upon separation between the two phases, the ethyl acetate solution was dried (anhydrous. Na$_2$SO$_4$) and evaporated under reduced pressure. To a solution of the protected ester (17.7 mmol) in 70 mL of anhydrous methanol at room temperature under an argon atmosphere was added p-toluenesulfonic acid monohydrate (0.34 g, 1.8 mmol). After stirring for 5 hours, aqueous sodium bicarbonate solution (50 mL) was added and the reaction mixture was evaporated under reduced pressure. Ethanol (50 mL) was added and the solution was again evaporated. The resultant material was purified via column chromatography to yield methyl 4-({2-[(5R)-5-(hydroxymethyl)-2-oxo pyrrolidin-1-yl]ethyl}thio) butanoate as a tan oil (0.17 g, mass spec. M+=275).

Step 2
Methyl 4-({2-[(2R)-2-formyl-5-oxopyrrolidin-1-yl]ethyl}thio)butanoate

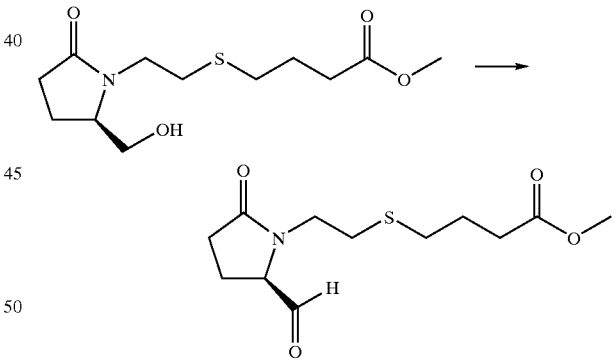

A solution of anhydrous dimethylsulfoxide (0.21 mL, 2.7 mmol) in 5 mL of methylene chloride under argon atmosphere was cooled to −70° C. and trifluoroacetic anhydride (0.17 mL, 1.2 mmol) in 1 mL of methylene chloride was added dropwise. The reaction was stirred for 15 minutes maintaining the temperature and then methyl 4-({2-[(5R)-5-(hydroxymethyl)-2-oxo pyrrolidin-1-yl]ethyl}thio) butanoate (0.15 g, 0.55 mmol) in 2 mL of methylene chloride was added. The solution was stirred and kept at −70° C. for 20 minutes followed by the addition of triethylamine (0.27 mL, 1.9 mmol). The reaction was allowed to come to room temperature, stirred for 30 minutes and then quenched with the addition of aqueous phosphoric acid solution (2%, 50 mL) and methylene chloride (25 mL). The reaction phases were separated and the combined organic layers were dried (Na₂SO₄) and evaporated under reduced pressure to yield methyl 4-({2-[(2R)-2-formyl-5-oxopyrrolidin-1-yl]ethyl}thio)butanoate which was taken on to next step.

Step 3
Methyl 4-[(2-{(5R)-2-oxo-5-[(1E)-3-oxooct-1-enyl]pyrrolidin-1-yl}ethyl)thio]-butanoate

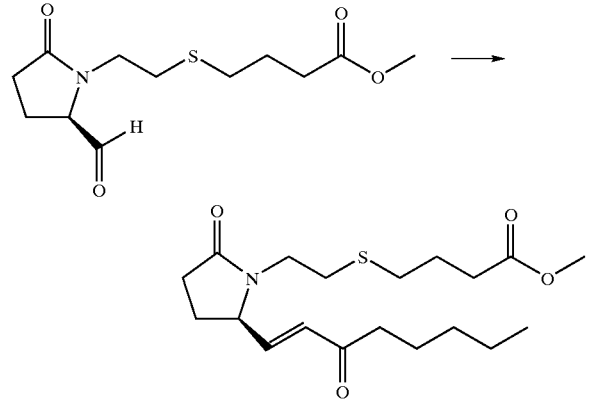

To a solution of sodium hydride (95%, 14 mg, 0.58 mmol) in 3 mL of anhydrous 1,2-dimethoxyethane at 0° C. under an argon atmosphere was added dimethyl 2-oxoheptylphosphonate (ACROS, 0.13 mL, 0.61 mmol). The cooling bath was removed and the reaction was stirred for 2 hours. After this time period, the mixture was cooled to 0° C. and a solution of methyl 4-({2-[(2R)-2-formyl-5-oxopyrrolidin-1-yl]ethyl}thio)butanoate (0.55 mmol) in anhydrous 1,2-dimethoxyethane was added. The reaction was allowed to come to room temperature, stirred for 2 hours and then quenched with an aqueous solution of saturated ammonium chloride. Ethyl acetate (50 mL) was then added and the mixture was partitioned between the two phases. The organic solution was dried (brine, Na₂SO₄), evaporated via reduced pressure and purified with column chromatography (SiO₂, EtOAc/Hexane-1/1) to yield methyl 4-[(2-{(5R)-2-oxo-5-[(1E)-3-oxooct-1-enyl]pyrrolidin-1-yl}ethyl)thio]-butanoate as an oil. This material was taken directly on to the next step.

Step 4
4-[(2-{(2R)-2-[(1E,3S)-3-Hydroxyoct-1-enyl]-5-oxopyrrolidin-1-yl}-ethyl)thio]butanoic acid Methyl Ester

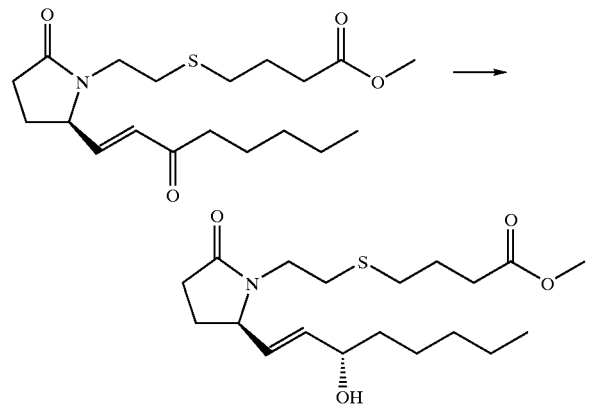

A solution of methyl 4-[(2-{(5R)-2-oxo-5-[(1E)-3-oxooct-1-enyl]pyrrolidin-1-yl}ethyl)thio]-butanoate (0.039 g, 0.1 mmol) in 2 mL of anhydrous toluene was added dropwise to a −30° C. solution of (R)-2-methyl-CBS-oxazaborolidine (1 M in toluene, 0.05 mL, 0.05 mmol) and borane-methyl sulfide complex (10 M, 0.01 mL, 0.1 mmol). The reaction was stirred for 7 hours at −30° C. and then a solution of hydrochloric acid in methanol (2 M, 1–2 mL) was added. The solution was warmed to room temperature and the solvents were removed via reduced pressure. The crude residue was purified via chromatography yielding 11 mg of 4-[(2-{(2R)-2-[(1E,3S)-3-hydroxyoct-1-enyl]-5-oxopyrrolidin-1-yl}ethyl)thio]butanoic acid methyl ester as an oil. This was taken directly on to the next step.

Step 5
4-[(2-{(2R)-2-[(1E,3S)-3-Hydroxyoct-1-enyl]-5-oxopyrrolidin-1-yl}ethyl)thio]butanoic Acid

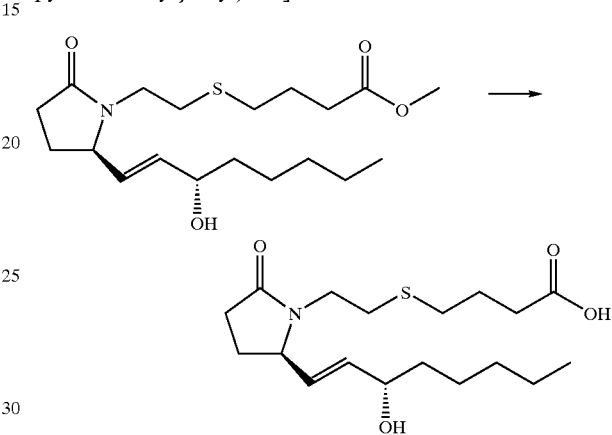

To a solution of 4-[(2-{(2R)-2-[(1E,3S)-3-hydroxyoct-1-enyl]-5-oxopyrrolidin-1-yl}ethyl)thio] butanoic acid methyl ester (0.011 g, 0.03 mmol) in 2 mL of methanol at room temperature under an argon atmosphere was added an aqueous solution of sodium hydroxide (1 M, 4–5 drops). The reaction was stirred for 4 hours, evaporated under reduced pressure and treated with aqueous hydrochloric acid (1 M) until acidic. The residue was diluted with water (10 mL) and extracted with ethyl acetate. The organic solution was dried (brine, Na₂SO₄) and evaporated to yield 7.5 mg of 4-[(2-{(2R)-2-[(1E,3S)-3-hydroxyoct-1-enyl]-5-oxopyrrolidin-1-yl}ethyl)thio]butanoic acid: ¹H NMR (300 MHz, CDCl₃) δ partial spectrum 5.74 (dd, 1H, J=5.7, 15.6 Hz), 5.53 (dd, 1 H, J=8.2, 15.6 Hz), 4.11–4.20 (m with apparent q, 2 H, J=6.0 Hz), 3.62–3.81 (m with dd, 2 H, J=2.4, 10.2 Hz), 3.08–3.20 (m, 1 H); MS m/z (M⁺), 357.

Similarly, following the procedure of Example 1 but replacing the appropriate reagents and steps will give compounds of the general formula I:
step 1 replacement of methyl 4-[(2-chloroethyl)thio]butanoate with methyl [(4-chlorobutyl)thio]acetate and sodium borohydride reduction in step 4 afforded {4-[2[R-(3-hydroxy-oct-1E-enyl)5-oxo-pyrrolidin-1-yl]butylsulfanyl}acetic acid, (2) ESMS: m/z (M⁺), 357,
replacement with [(4-chlorobutyl)thio]acetic acid methyl ester in step 1 gives {4-[2[R-(1E-3S-3-hydroxy-oct-1-enyl)5-oxo-pyrrolidin-1-yl]butylsulfanyl}acetic acid, (3) ESMS: m/z (M⁺), 357,
replacement with (4-bromo-butyloxy)-acetic acid ethyl ester in step 1 gives {4-[(R)-2-((E)-3-hydroxy-oct-1-enyl)-5-oxo-pyrrolidin-1-yl]-butoxy}-acetic acid, (4) MS: m/z (M⁺), 341,
dimethyl 2-oxoheptylphosphonate is replaced with [2-(5-trifluoromethyl-furan-2-yl)-2-oxo-ethyl]phosphonic acid dimethyl ester (in-turn prepared according to Example 5)

in step 3 gives (4-{(R)-2-[(E)-3-hydroxy-3-(5-trifluoromethyl-furan-2-yl)-propenyl]-5-oxo-pyrrolidin-1-yl}-butylsulfanyl)-acetic acid, (5) MS: m/z (M$^{+1}$) 422, 4-[(2-{(2R)-2-[(1E,3S)-3-hydroxy-oct-1-enyl]-5-oxopyrrolidin-1-yl}-ethyl)thio]butanoic acid methyl ester upon exposure to in a −20° C. dichloromethane solution of 3-chloroperbenzoic acid and hydrolysis as step 5, gives 4-{2-[(R)-2-((S)-(E)-3-hydroxy-oct-1-enyl)-5-oxo-pyrrolidin-1-yl]-ethanesulfinyl}-butyric acid,(6) MS: m/z (M$^{+1}$) 374, 4-[(2-{(2R)-2-[(1E,3S)-3-hydroxy-oct-1-enyl]-5-oxopyrrolidin-1-yl}-ethyl)thio]butanoic acid methyl ester upon exposure to a 0° C. aqeuous methanol suspension of OXONE® gives 4-{2-[(R)-2-((S)-(E)-3-hydroxy-oct-1-enyl)-5-oxo-pyrrolidin-1-yl]-ethanesulfonyl}-butyric acid, (7) MS: m/z (M$^{+1}$) 390.

Example 2

{(Z)-4-[(R)2-((E)-3-Hydroxy-oct-1-enyl)-5-oxo-pyrrolidin-1-yl]-but-2-enyloxy}-acetic Acid (8)

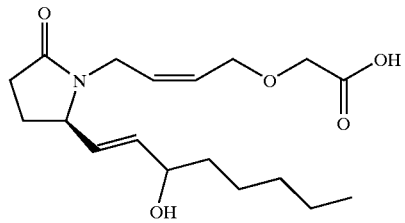

Step 1
[(Z)-4-((R)-2-Hydroxymethyl-5-oxo-pyrrolidin-1-yl)-but-2-enyloxy]-acetic Acid Ethyl Ester

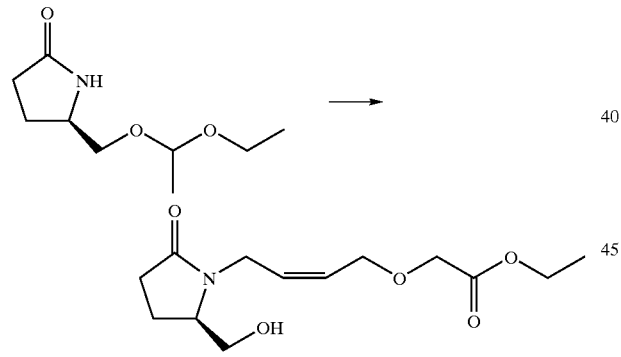

To a solution of (5R)-5-(1-ethoxyethoxymethyl)pyrrolidin-2-one (2.5 g, 13.4 mmol) in 10 mL of anhydrous dimethylformamide (DMF) at 0° C. under an argon atmosphere was added a solution of sodium hydride (95%, 0.32 g, 13.4 mmol) in 40 mL of DMF. The cooling bath was removed and the reaction was stirred for 60 minutes. A solution of potassium iodide (2.2 g, 13.4 mmol) and Z-4-chloro-but-2-enyloxy)-acetic acid ethyl ester (2.7 g, 21.3 mmol) in 5 mL DMF was added and the reaction solution was allowed to come to room temperature, and stirred overnight. A saturated solution of NaHCO$_3$ was added and the solution was extracted, dried (brine wash, anhydrous. Na$_2$SO$_4$) and evaporated under reduced pressure.

To a solution of the protected ester (1.8 g, 5.24 mmol) in 20 mL of anhydrous methanol at room temperature under an argon atmosphere was added p-toluenesulfonic acid monohydrate (0.1 g, 5.5 mmol). After stirring overnight, aqueous sodium bicarbonate solution (50 mL) was added and the reaction mixture was extracted, dried, concentrated and purified by chromatography to yield [(Z)-4-((R)-2-hydroxymethyl-5-oxo-pyrrolidin-1-yl)-but-2-enyloxy]-acetic acid ethyl ester.

Step 2
[(Z)-4-((R)-2-Formyl-5-oxo-pyrrolidin-1-yl)-but-2-enyloxy]-acetic.acid Ethyl Ester

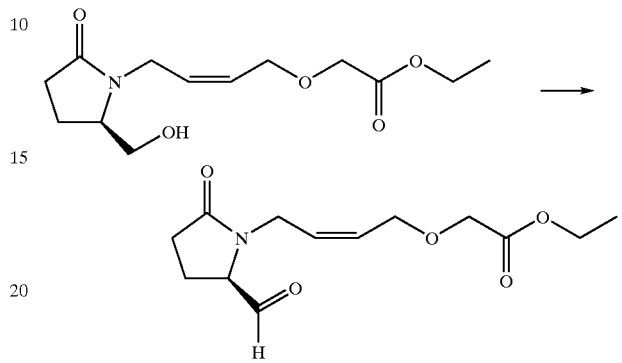

A solution of anhydrous dimethylsulfoxide (0.45 mL, 5.7 mmol) in 5 mL of methylene chloride under nitrogen atmosphere was cooled to −78° C. and trifluoroacetic anhydride (0.68 mL, 4.8 mmol) in 2 mL of methylene chloride was added dropwise. The reaction was stirred for 15 minutes maintaining the temperature and then [(Z)-4-((R)-2-hydroxymethyl-5-oxo-pyrrolidin-1-yl)-but-2-enyloxy]-acetic acid ethyl ester (0.62 g, 2.3 mmol) in 20 mL of methylene chloride was added. The solution was stirred and kept at −70° C. for 20 minutes followed by the addition of triethylamine (0.96 mL, 6.9 mmol). The reaction was allowed to come to room temperature, stirred for 30 minutes and then quenched with the addition of aqueous ammonium chloride solution. The reaction phases were separated and the organic layer was dried (brine, Na$_2$SO$_4$), concentrated and purified by chromatography to yield [(Z)-4-((R)-2-formyl-5-oxo-pyrrolidin-1-yl)-but-2-enyloxy]-acetic.acid ethyl ester which was taken on to next step.

Step 3
{(Z)-4-[(R)-2-Oxo-5-((E)-3-oxo-oct-1-enyl)-pyrrolidin-1-yl]-but-2-enyloxy}-acetic Acid Ethyl Ester

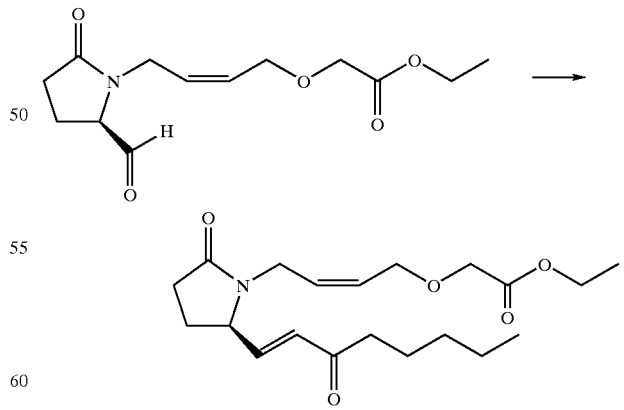

To a solution of sodium hydride (95%, 0.02 g, 0.78 mmol) in 10 mL of anhydrous 1,2-dimethoxyethane at 0° C. under a nitrogen atmosphere was added dimethyl 2-oxoheptylphosphonate (0.17 mL, 0.78 mmol), and the reaction was stirred for 1 hour. A solution of [(Z)-4-((R)-2- formyl-5-oxo-pyrrolidin-1-yl)-but-2-enyloxy]-acetic acid ethyl ester (0.21 g, 0.78 mmol) in 2 mL anhydrous 1,2-dimethoxyethane was added. The reaction was allowed to come to room temperature, stirred for 3 hours and then quenched with an aqueous solution of saturated ammonium chloride. After extraction with ethyl acetate, the organic solution was dried (brine, Na$_2$SO$_4$), evaporated and purified by chromatography to yield {(Z)-4-[(R)-2-oxo-5-((E)-3-oxo-oct-1-enyl)-pyrrolidin-1-yl]-but-2-enyloxy}-acetic acid ethyl ester as an oil. This material was taken directly on to the next step.

Step 4
{(Z)-4-[(R)-2-((E)-3-Hydroxy-oct-1-enyl)-5-oxo-pyrrolidin-1-yl]-but-2-enyloxy}-acetic Acid Ethyl Ester

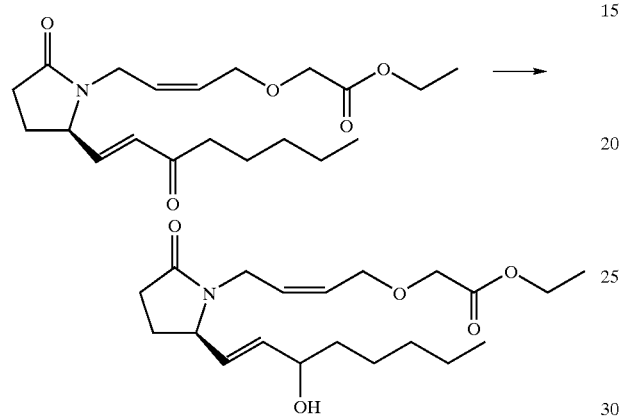

A solution of {(Z)-4-[(R)-2-oxo-5-((E)-3-oxo-oct-1-enyl)-pyrrolidin-1-yl]-but-2-enyloxy}-acetic acid ethyl ester (0.7 g, 1.97 mmol) in 15 mL of ethanol was stirred at 0° C., and 0.082 g NaBH$_4$ was added. The reaction was allowed to come to room temperature and stirred for 7 hours, followed by addition of a solution of hydrochloric acid in methanol (2 M, 1–2 mL) and extraction with ethyl acetate. The organic phase was dried, concentrated, purified via chromatography to yield {(Z)-4-[(R)-2-((E)-3-hydroxy-oct-1-enyl)-5-oxo-pyrrolidin-1-yl]-but-2-enyloxy}-acetic acid ethyl ester, and taken directly on to the next step.

Step 5
{(Z)-4-[(R)-2-((E)-3-Hydroxy-oct-1-enyl)-5-oxo-pyrrolidin-1-yl]-but-2-enyloxy}-acetic Acid

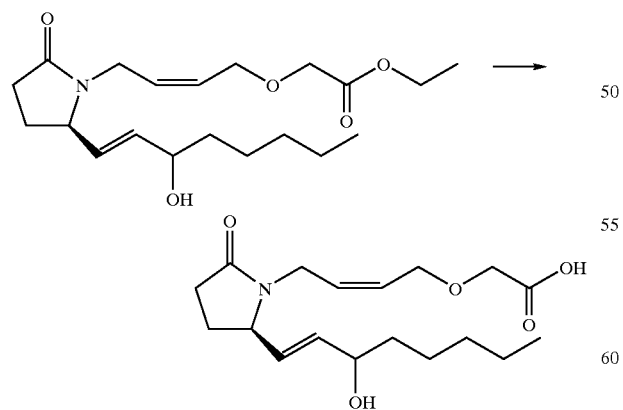

To a solution of {(Z)-4-[(R)-2-((E)-3-hydroxy-oct-1-enyl)-5-oxo-pyrrolidin-1-yl]-but-2-enyloxy}-acetic acid ethyl ester (0.22 g, 0.6 mmol) in a mixture of 5 mL of methanol and 5 mL THF at room temperature under a nitrogen atmosphere was added an aqueous solution of lithium hydroxide (0.1 g, 2.4 mmol) in 3 mL of water. The reaction was stirred at 45° C. overnight, cooled to room temperature and treated with aqueous hydrochloric acid (1 M) until acidic. The residue was diluted with water (10 mL) and extracted with ethyl acetate. The organic solution was dried (brine, Na$_2$SO$_4$) and evaporated to yield {(Z)-4-[(R)-2-((E)-3-hydroxy-oct-1-enyl)-5-oxo-pyrrolidin-1-yl]-but-2-enyloxy}-acetic acid; ESMS m/Z M$^+$, 339.

Example 3

{4-[(R)-2-((E)-(S)-3-Hydroxy-oct-1-enyl)-5-oxo-pyrrolidin-1-yl]-butoxy}-acetic Acid (9)

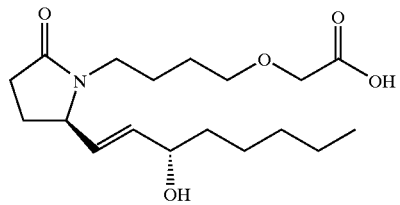

Step 1
{4-[(R)-2-((E)-(S)-3-Hydroxy-oct-1-enyl)-5-oxo-pyrrolidin-1-yl]-butoxy}-acetic Acid Methyl Ester

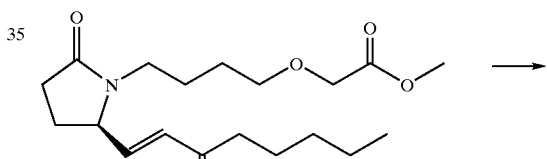

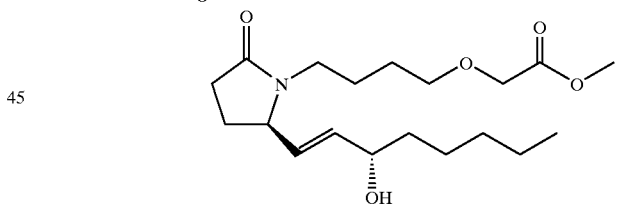

A solution of the {4-[(R)-2-Oxo-5-((E)-3-oxo-oct-1-enyl)-pyrrolidin-1-yl]-butoxy}-acetic acid methyl ester prepared as in Example 1 (250 mg, 0.71 mmol) in 10 mL of anhydrous toluene was added dropwise to a −26° C. solution of (R)-2-methyl-CBS-oxazaborolidine (Aldrich, 1 M in toluene, 0.35 mL) and borane-methyl sulfide complex (10 M, 0.07 mL). The reaction was stirred under nitrogen for 7 hours at −26° C. and then a solution of hydrochloric acid in methanol (2 M, 1-2 mL) was added. The solution was warmed to room temperature and the solvents were removed via reduced pressure. The crude residue was purified via silica gel chromatography yielding 11 mg of {4-[(R)-2-((E)-(S)-3-hydroxy-oct-1-enyl)-5-oxo-pyrrolidin-1-yl]-butoxy}-acetic acid methyl ester as an oil. This was taken directly on to the next step.

Step 2

{4-[(R)-2-((E)-(S)-3-Hydroxy-oct-1-enyl)-5-oxo-pyrrolidin-1-yl]-butoxy}-acetic Acid

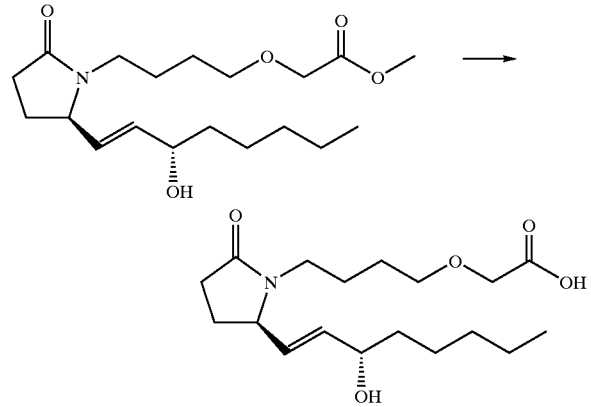

To a solution of {4-[(R)-2-((E)-(S)-3-hydroxy-oct-1-enyl)-5-oxo-pyrrolidin-1-yl]-butoxy}-acetic acid methyl ester (0.14 g, 0.4 mmol) in a mixture of 2 mL of methanol and 2 mL THF at room temperature under a nitrogen atmosphere was added an aqueous solution of lithium hydroxide (0.066 g, 1.6 mmol) in 1 mL of water. The reaction was stirred at 45° C. overnight, cooled to room temperature and treated with aqueous hydrochloric acid (1 M) until acidic. The residue was diluted with water (10 mL) and extracted with ethyl acetate. The organic solution was dried (brine, $Na_2SO_4$), evaporated and purified by chromatography to yield 28 mg of {4-[(R)-2-((E)-(S)-3-hydroxy-oct-1-enyl)-5-oxo-pyrrolidin-1-yl]-butoxy}-acetic acid; ESMS: m/z ($M^+$) 341.

Similarly, following the procedures of Example 3 but replacing the appropriate reagents will give compounds of the general formula I:

Replacement with {4-[(R)-2-Oxo-5-[(E)-3-oxo-4-(3-trifluoromethyl-phenyl)-but-1-enyl]-pyrrolidin-1-yl]-butoxy}-acetic acid ethyl ester in step 1 gives (4-{(R)-2-[(S)-(E)-3-hydroxy-4-(3-trifluoromethyl-phenyl)-but-1-enyl]-5-oxo-pyrrolidin-1-yl}-butoxy)-acetic acid, (10) MS: m/z ($M^{+1}$) 430, Replacement with {4-[(R)-2-Oxo-5-[(E)-3-(2'-methyl-biphenyl-3-yl)-3-oxo-prop-1-enyl]-pyrrolidin-1-yl]-butoxy}-acetic acid ethyl ester gives and of (R)-2-methyl-CBS-oxazaborolidine/borane-dimethyl sulfide with sodium borohydride-cerium (III) chloride in step 1, (4-{(R)-2-[(E)-3-hydroxy-3-(2'-methyl-biphenyl-3-yl)-propenyl]-5-oxo-pyrrolidin-1-yl}-butoxy)-acetic acid, (11) MS: m/z ($M^{+1}$) 438, Replacement of {4-[(R)-2-Oxo-5-[(E)-3-(4'-chloro-biphenyl-3-yl)-3-oxo-pro-1-enyl]-pyrrolidin-1-yl]-butoxy}-acetic acid ethyl ester in step 1 gives (4-{(R)-2-[(E)-3-(4'-chloro-biphenyl-3-yl)-3-hydroxy-propenyl]-5-oxo-pyrrolidin-1-yl}-butoxy)-acetic acid, (12) MS: m/z ($M^{+1}$) 459.

Example 4

4-{2-[(R)-2-((E)-3-Hydroxy-3-pentyl-oct-1-enyl)-5-oxo-pyrrolidin-1-yl]-ethylsulfanyl}-butyric Acid (13), Step 1:

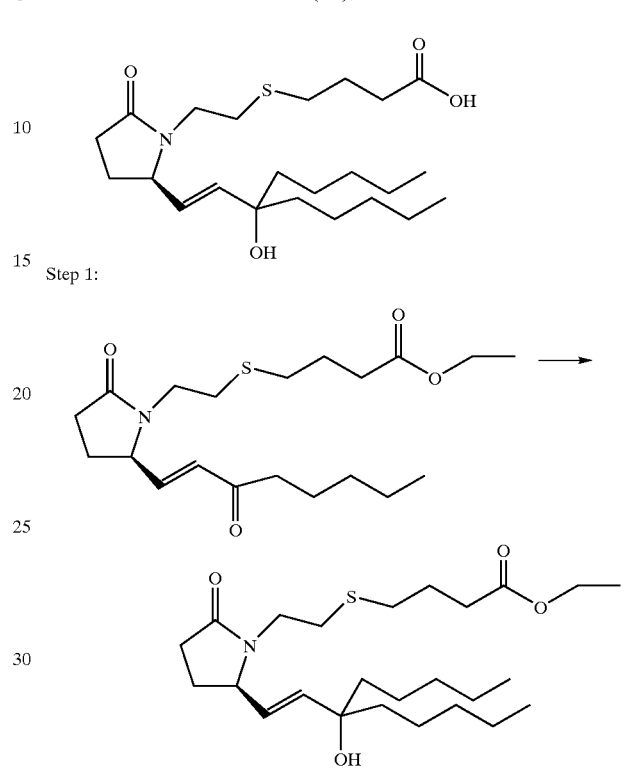

To a -24° C. tetrahydrofuran (38 mL) solution of enone (from Example 1, step 3, 1.52 g) was treated with n-pentylmagnesium bromide (1.8 mL, 2 M ether solution from Aldrich). After 1 hour, the mixture was poured into aqueous ammonium chloride and extracted with ethyl acetate. Following drying and filtration, the desired alcohol (780 mg) was obtained after silica gel chromatography (elute with 5% methanol in ethyl acetate).

Step 2:

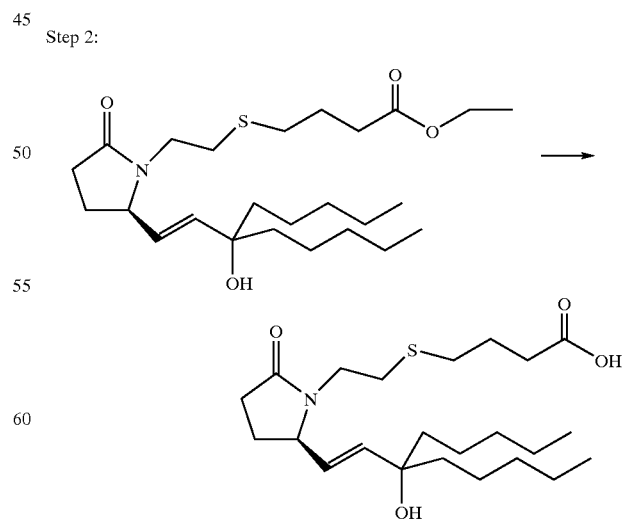

The ester (273 mg) was dissolved in tetrahydrofuran (6 mL) and water (1.2 mL) and treated with LiOH $H_2O$ (126 mg). After stirring at ambient temperature for 16 hours, the mixture was partitioned between water and ethyl ether. The aqueous layer was rendered acidic with glacial acetic acid and extracted with ethyl acetate. The ethyl acetate extracts were combined, dried over sodium sulfate, and filtered. The title acid (215 mg) was obtained as an oil, MS: m/z ($M^{+1}$) 428.

Similarly, following the procedure of Example 4 but replacing the appropriate reagents and steps will give compounds of the general formula I:
Replacement of normal-pentylmagnesium bromide with methylmagnesium bromide in step 1 gives 4-{2-[(R)-2-((E)-3-hydroxy-3-methyl-oct-1-enyl)-5-oxo-pyrrolidin-1-yl]-ethylsulfanyl}-butyric acid, (14) MS: m/z ($M^{+1}$) 372.

Preparation 5

{2-[3-(3-Fluorophenoxy)-phenyl]-2-oxo-ethyl}phosphonic Acid Dimethyl Ester

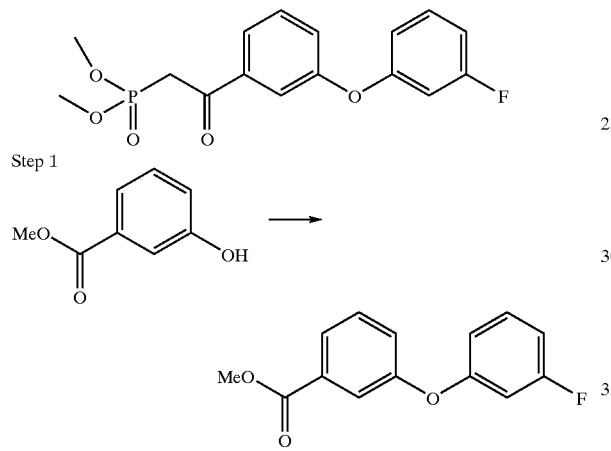

Step 1

A suspension of methyl 3-hydroxybenzoic acid (5.4 g, 35.5 mmol), 3-fluorophenylboronic acid (5.5 g, 35.5 mmol), cupric acetate (7.1 g, 35.5 mmol), 3 Å molecular sieves (9 g), pyridine (12 mL, 145 mmol) in dichloromethane (220 mL) was stirred at ambient temperature under ambient atmosphere. After 11 days, the mixture was filtered through Celite® and the volatiles were removed from the filtrate. The desired ester (3.68 g) was eluted from silica gel column with 5:1 hexane:ethyl acetate and taken onto the next step.

Step 2

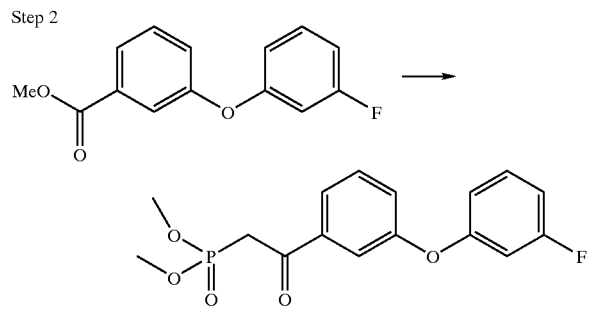

A tetrahydrofuran (100 mL) solution of dimethyl methylphosphonate (4.0 mL, 37.5 mmol) was cooled to −78° C. under argon and treated with normal butyllithium (15.0 mL, 2.5 M hexane solution, 37.5 mmol) and allowed to stir for 45 minutes. The ester obtained from step 1 (4.62 g, 18.7 mmol) was dissolved in tetrahydrofuran (15 mL) and added to the solution above at −78° C. and the resulting mixture was stirred at 0° C. for 1 hour. At which time, the yellow solution was partitioned between aqueous ammonium chloride (100 mL) and ethyl ether (200 mL). The organic portion was washed with fresh water (3×30 mL), then brine, and stored over anhydrous sodium sulfate. Following filtration and removal of the volatiles in vacuo, the desired β-ketophosphonate (5.8 g) was obtained as a viscous oil: $^1$H NMR (300 MHz, $CDCl_3$) δ7.78 (dt, J=0.6, 0.9, 7.8 Hz, 1 H), 7.63 (t, J=2.1 Hz, 1 H), 7.48 (t, J=8.1 Hz, 1 H), 7.32–7.26 (m, 2 H), 6.90–6.78 (m, 2 H), 6.70 (dt, J=2.4, 9.9 Hz, 1 H), 3.80 (d, J=11.2 Hz, 6 H), 3.61 (d,J=22.6 Hz,2 H).

Example 5

4-[2-((S)-2-{(R)-3-[3-(3-Fluoro-phenoxy)-phenyl]-3-hydroxy-propyl}-5-oxo-pyrrolidin-1-yl)-ethylsulfanyl]-butyric Acid (15)

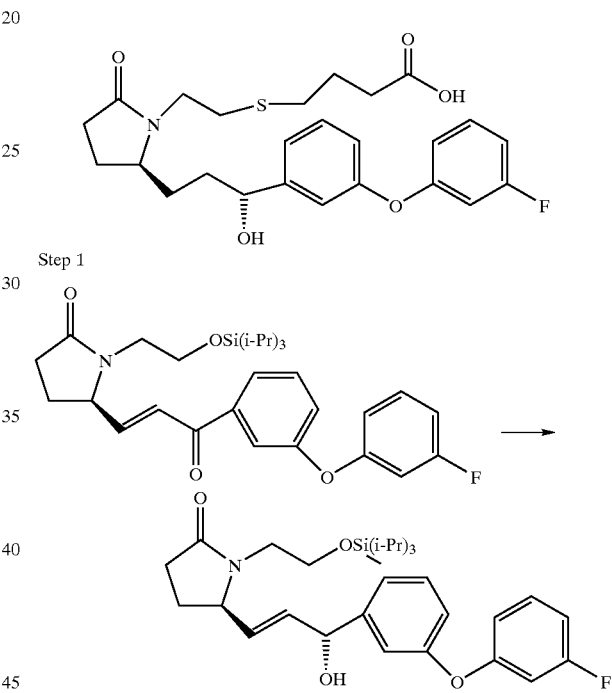

Step 1

An ambient temperature ethyl acetate (70 mL) solution of the enone (950 mg, 1.8 mmol) was treated with 10% palladium on carbon (150 mg) and stirred vigorously under ambient pressure of hydrogen gas. After 90 minutes, the suspension was filtered through Celite® and the volatiles were removed from the filtrate in vacuo. The residue (945 mg) was dissolved in anhydrous toluene (10 mL) and added to a premixed 0° C. solution of (S)-2-methyl-CBS-oxazaborolidine (0.20 mL, 1 M toluene solution from Aldrich), anhydrous toluene (20 mL), and borane dimethyl sulfide complex (0.25 mL, 5 M ethyl ether solution). The yellow solution was stirred at 0° for 1.3 h and treated with hydrochloric acid (1 mL, 2 M methanol solution). The volatiles were removed with a rotary evaporator and 10 mL of methanol was added. The volatiles were removed again and replaced with 20 mL of toluene and removed again. The resultant white paste was subjected to silica gel chromatography. The desired alcohol (620 mg, 1.2 mmol) was eluted with a gradient of 2-propanol (2–4%) in 2:1 hexane:ethyl acetate.

Step 2

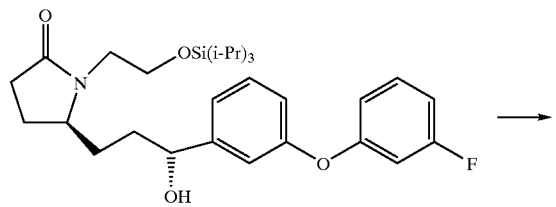

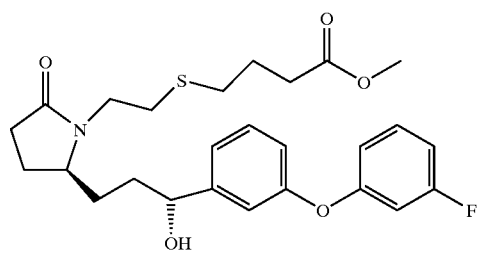

An ambient temperature tetrahydrofuran (5 mL) solution of silyl ether (620 mg, 1.2 mmol) was treated with tetrabutylammonium fluoride hydrate (443 mg, 1.4 mmol). The solution was stirred for 2.5 h, diluted with 10 mL hexane and loaded onto a pad of silica. The desired diol (380 mg) was eluted with 5–10% ethanol in ethyl acetate and obtained as a glass. The diol (375 mg) was dissolved in tetrahydrofuran (10 mL) and cooled to −20° C. under Argon. It was sequentially treated with triethylamine (0.17 mL) and methanesulfonyl chloride (0.08 mL) which resulted in a suspension. In a separate vessel, a solution of anhydrous methanol (1 mL) and anhydrous tetrahydrofuran (5 mL) under argon was treated with potassium t-butoxide (3.0 mL, 1 M tetrahydrofuran solution, Aldrich) and the slightly warm solution was stirred for 10 min. γ-Thiobutyrolactone (0.21 mL, 2.5 mmol, Aldrich) was added in one portion and stirred at ambient temperature for 5 minutes and the suspension of the mesylate was added via cannula to the potassium thiolate solution. The mixture was stirred for 1 h at ambient temperature and then partitioned between aqueous ammonium chloride and ethyl acetate (4×25 mL). The combined organic extracts were stored over anhydrous sodium sulfate, and the volatiles were removed with a rotary evaporator. The desired ester (350 mg) was obtained following elution from silica gel chromatography with 4:1 ethyl acetate:hexane as an oil: ESMS: m/z M$^{+1}$, 490.

Step 3

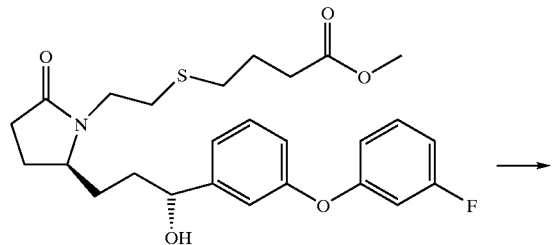

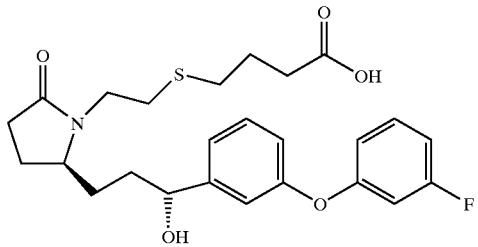

A methanol (10 mL) solution of the ester (350 mg, 0.72 mmol) was treated with sodium hydroxide (0.5 mL, 5 M aqueous) and stirred at ambient temperature for 4–5 h. The volatiles were removed under a stream of nitrogen and the mixture was partitioned between water and ethyl ether. The aqueous layer was rendered acidic with hydrochloric acid (12 M aqueous) and extracted with ethyl acetate (4×15 mL). The combined organic extracts were stored over anhydrous sodium sulfate. The desired acid (299 mg) was obtained following filtration and removal of the volatiles as an oil: $^1$H NMR (300 MHz, CDCl$_3$, partial spectrum) δ7.39–7.20 (m, 2 H), 7.10 (d, J=7.8 Hz, 1 H), 7.03 (t, J=1.2 Hz, 1 H), 6.83–6.76 (m, 2 H), 6.67 (dt, J=2.4, 10.2 Hz,1 H), 4.75 (dd, J=6.7, 12.3 Hz, 1 H), 3.78–3.52 (m, 2 H), 2.46 (t, J=6.9 Hz, 2 H); MS: m/z M$^{+1}$, 476.

Similarly, following the procedures of Example 5 but replacing the appropriate reagents and steps will give compounds of the general formula I:

Replacement with (R)-5-{(E)-3-oxo-oct-1-enyl}-1-(2-triisopropylsilyloxy-ethyl)-pyrrolidin-2-one in step 1 gives, with the exclusion of catalytic hydrogenation and the replacement of (S)-2-methyl-CBS-oxazaborolidine with (R)-2-methyl-CBS-oxazaborolidine and the subsequent use of methyl 4-mercapto-3-methyl butyrate in step 2, 4-{2-[(R)-2-((S)-(E)-3-hydroxy-oct-1-enyl)-5-oxo-pyrrolidin-1-yl]-ethylsulfanyl}-3-methyl-butyric acid, (16) MS: M/z (M$^{+1}$) 372;

Use of (R)-5-{(E)-3-oxo-oct-1-enyl}-1-(2-triisopropylsilyloxy-ethyl)-pyrrolidin-2-one in step 1 gives, with the use of methyl 4-mercapto-2-methyl butyrate in step 2, 4-{2-[(R)-2-((S)-(E)-3-hydroxy-oct-1-enyl)-5-oxo-pyrrolidin-1-yl]-ethylsulfanyl}-2-methyl-butyric acid, (17) MS: m/z (M$^{+1}$) 372, Use of (R)-5-{(E)-3-oxo-oct-1-enyl}-1-(2-triisopropylsilyloxy-ethyl)-pyrrolidin-2-one in step 1 gives, with the use of methyl 4-mercapto-4-methyl butyrate in step 2, 4-{2-[(R)-2-((S)-(E)-3-hydroxy-oct-1-enyl)-5-oxo-pyrrolidin-1-yl]-ethylsulfanyl}-4-methyl-butyric acid, (18) MS: m/z (M$^{+1}$) 372, Use of (R)-5-{(E)-3-oxo-oct-1-enyl}-1(2-triisopropylsilyloxy-ethyl)-pyrrolidin-2-one in step 1 gives, with the use of methyl 4-mercapto-2-butenyrate in step 2, 4-{2-[(R)-2-((S)-(E)-3-hydroxy-oct-1-enyl)-5-oxo-pyrrolidin-1-yl]-ethylsulfanyl}-2-butenyric acid, (19) MS: m/z (M$^{+1}$) 356, (R)-5-{(E)-3-oxo-oct-1-enyl}-1-(2-triiso-propylsilyloxy-ethyl)-pyrrolidin-2-one in step 1 gives, with the use of methyl 2-[1-(mercaptomethyl)cyclopropyl]acetate in step 2, (1-{2-[(R)-2-((S)-(E)-3-hydroxy-oct-1-enyl)-5-oxo-pyrrolidin-1-yl]-ethylsulfanylmethyl}-cyclopropyl)-acetic acid, (20) MS: m/z (M$^{+1}$) 384;

(R)-5-{(E)-3-oxo-oct-1-enyl}-1-(2-triiso-propylsilyloxy-ethyl)-pyrrolidin-2-one gives, with the use of methyl thioglcolate in step 2, 5-{2-[(R)-2-((S)-(E)-3-hydroxy-oct-1-enyl)-5-oxo-pyrrolidin-1-yl]-ethylsulfanyl}-acetic acid, (21) MS: m/z (M$^{+1}$) 330,

- (R)-5-{(E)-3-oxo-oct-1-enyl}-1-(2-triiso-propylsilyloxy-ethyl)-pyrrolidin-2-one with the use of methyl 3-mercaptopropionate in step 2 and the use of Lipase type in step 3 gives, 3-{2-[(R)-2-((S)-(E)-3-hydroxy-oct-1-enyl)-5-oxo-pyrrolidin-1-yl]-ethylsulfanyl}-propionic acid, (22) MS: m/z (M$^{+1}$) 344,
- (R)-5-{(E)-3-oxo-oct-1-enyl}-1-(2-triiso-propylsilyloxy-ethyl)-pyrrolidin-2-one gives, with the use of methyl 5-mercaptopentanoate in step 2 gives, 5-{2-[(R)-2-((S)-(E)-3-hydroxy-oct-1-enyl)-5-oxo-pyrrolidin-1-yl]-ethylsulfanyl}-pentanoic acid, (23) MS: m/z (M$^{+1}$) 372,
- Use of (R)-5-{(E)-3-[3-(4'chloro-2'-methylphenyl)-phenyl]-3-oxo-propyl}-1-(2-triiso-propylsilyloxy-ethyl)-pyrrolidin-2-one in step 1 gives 4-[2-((S)-2-{(R)-3-[3-(4'chloro-2'-methylphenyl)-phenyl]-3-hydroxy-propyl}-5-oxo-pyrrolidin-1-yl)-ethylsulfanyl]-butyric acid (24) MS: m/z (M$^{+1}$) 491;
- Use of (R)-5-{(E)-3-[3-(4'chloro-2'-methylphenyl)-phenyl]-3-oxo-propyl}-1-(2-triiso-propylsilyloxy-ethyl)-pyrrolidin-2-one and (R)-2-methyl-CBS-oxazaborolidine in step 1 gives 4-[2-((S)-2-{(S)-3-[3-(4'-chloro-2'-methylphenyl)-phenyl]-3-hydroxy-propyl}-5-oxo-pyrrolidin-1-yl)-ethylsulfanyl]-butyric acid (25), MS: m/z (M$^{+1}$) 491,
- Use of (R)-5-{(E)-3-[3-(2',4'-difluorophenyl)-phenyl]-3-oxo-propyl}-1-(2-triiso-propylsilyloxy-ethyl)-pyrrolidin-2-one and (S)-2-methyl-CBS-oxazaborolidine in step 1 gives 4-[2-((S)-2-{(R)-3-[3-(3-(2',4'-difluorophenyl)-phenyl]-3-hydroxy-propyl}-5-oxo-pyrrolidin-1-yl)-ethylsulfanyl]-butyric acid (26), MS: m/z (M$^{+1}$) 478,
- (R)-5-{(E)-3-[3-(4'-methoxy-2'-methylphenyl)-phenyl]-3-oxo-propyl}-1-(2-triiso-propylsilyloxy-ethyl)-pyrrolidin-2-one and (S)-2-methyl-CBS-oxazaborolidine in step 1 gives 4-[2-((S)-2-{(R)-3-[3-(3-(4'-methoxy-2'-methyl)-phenyl]-3-hydroxy-propyl}-5-oxo-pyrrolidin-1-yl)-ethylsulfanyl]-butyric acid (27), MS: m/z (M$^{+1}$) 486,

Example 6

6-[2-((S)-(E)-3-Hydroxy-oct-1-enyl)-5-oxo-pyrrolidin-1-yloxy]-hexanoic acid (28)

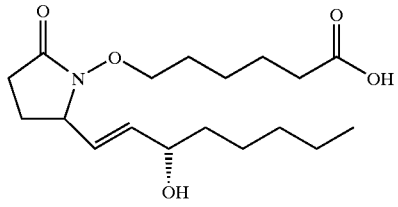

Step 1

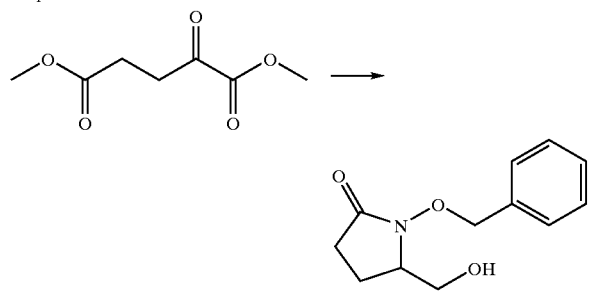

Dimethyl 2-(O-benzyloxyamino)glutarate (4.7 g, 16.7 mmol, prepared from dimethyl 2-oxoglutarate using the methods described in C. Fuganti et al., *J. Org. Chem.*, 49, 543–546) was dissolved in dry tetrahydrofuran (170 ml) and cooled in an ice bath. Iso-propylmagnesium chloride (8.35 mL of 2 M tetrahydrofuran solution) was added slowly. The reaction was stirred while warming to rt over a period of 16 h. The reaction was quenched by addition of a saturated ammonium chloride solution and water and partitioned with ethyl acetate. The layers were separated and the aqueous layer was extracted once more with ethyl acetate. The combined organic layers were washed with brine and dried over sodium sulfate. After filtration and concentration, the residue was chromatographed on silica gel (230–400 mesh) using 30% ethyl acetate/hexanes. Product fractions were collected to give 2.85 g of ethyl 1-benzyloxy-5-pyrrolidinone-2-carboxylate as a white solid. This method has been previously described for intermolecular amidations: J. M. Williams et al., *Tet. Lett.*, 36(31), 5461–5464. Selective reduction of ethyl 1-benzyloxy-5-pyrrolidinone-2-carboxylate as described in: M. Miller et al., *J. Org. Chem.*, 47, 4928–4933, gave 1-benzyloxy-5-hydroxymethyl-2-pyrrolidinone, MS: m/z 222 (M$^{+1}$); mp 121–123° C.

Step 2

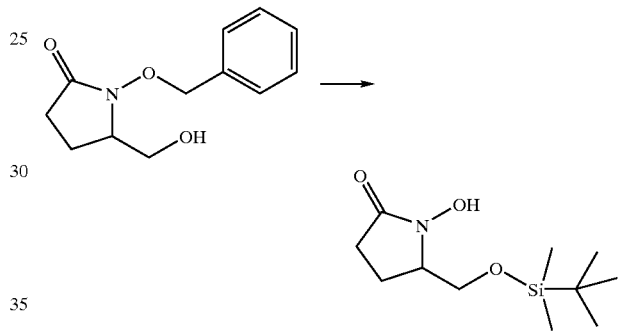

1-Benzyloxy lactam (1.1 g, 4.97 mmol) was dissolved in dry DMF (12 mL) and cooled in an ice bath. Imidazole (0.37 g, 5.5 mmol) and then tert-butyldimethylsilyl chloride (0.97 g, 6.46 mmol) were added. The ice bath was removed and the reaction was stirred at room temperature for 2.5 hours. Ethyl acetate and water were added and the layers were separated. The organic layer was washed with 0.5 M HCl twice, water and sat. NaHCO$_3$ solution. The organic layer was dried over sodium sulfate, filtered and concentrated. The residue was chromatographed on silica gel (230–400 mesh) using 25%–35% ethyl acetate/hexanes. Concentration of product fractions yielded 1.54 g of an oil. The oil was dissolved in 20% tetrahydrofuran/ethanol (20 ml), 1.9 g 10% Pd on carbon was added, and the reaction was stirred under a hydrogen atmosphere (1 atm) for 2 hours. The reaction was purged with nitrogen, filtered through Celite, and concentrated to give 1.1 g of the desired hydroxymate lactam: MS m/z 246 (M$^{+H}$) which was used without further purification.

Step 3

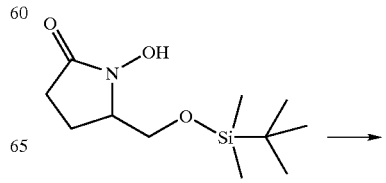

-continued

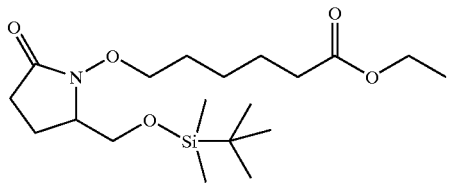

Potassium iodide (crushed, 0.89 g, 1.2 mmol) and sodium hydride (60% dispersion in mineral oil, 0.2 g, 1.1 mmol) were added to dry DMF (11 mL). The mixture was cooled in an ice bath and a solution of hydroxymate lactam (1.1 g, 4.47 mmol) in 6 mL of DMF was added dropwise. The reaction was stirred for 10 minutes and a solution of ethyl 6-bromohexanonate (Aldrich, 0.95 mL, 1.2 mmol) in 5 mL of DMF was added slowly. The ice bath was removed and the reaction was placed in a 50° C. bath for 16 hours. Saturated ammonium chloride solution, water and ethyl acetate were added and the organic layer was separated. The aqueous layer was extracted once more with ethyl acetate and the combined organic layers were washed with water and brine solution, dried over sodium sulfate and concentration. The residue was chromato graphed on silica gel using 40% ethyl acetate/hexanes to give 1.45 g of the ethyl ester as a clear oil: MS: m/z 388 ($M^{+1}$).

Step 4

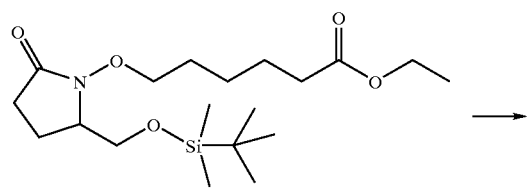

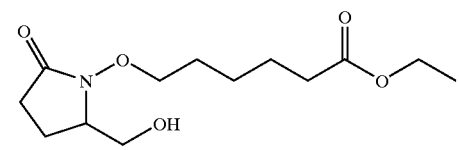

To an ice cold solution silyl ether (1.4 g, 1.44 mmol) in 18 ml of dry tetrahydrofuran was added tetrabutylammonium fluoride (9.3 mL of 1 M THF solution). The reaction was stirred for 10 minutes, the ice bath was removed, and the reaction was stirred at rt for 2 h. The reaction was cooled in an ice bath and ethyl acetate, ammonium chloride solution and water were added. The layers were separated and the aqueous layer was extracted once more with ethyl acetate. The combined organic layers were dried over sodium sulfate, evaporated, and the residue was chromatographed on silica gel using 3% methanol/dichloromethane to give the hydroxymethyl compound (970 mg) as a clear oil: MS m/z 274 ($H^+$).

Step 5

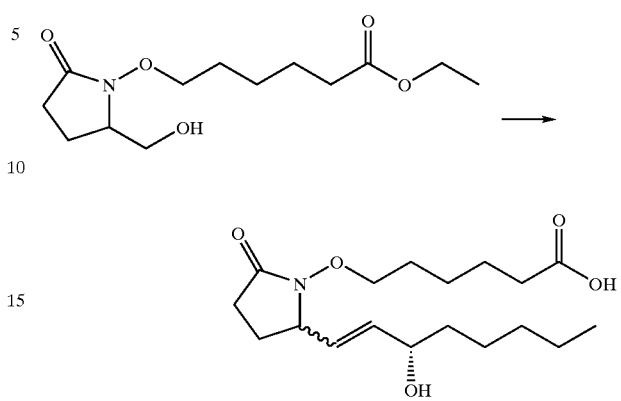

Individual diastereomers were separated following the enone reduction step (as described in Example 3, step 1 (using R-2-methyl CBS reagent and then silica gel chromatography). More polar 12-diastereomer: 6-[2-((3S)-(E)-3-Hydroxy-oct-1-enyl)-5-oxo-pyrrolidin-1-yloxy]-hexanoic acid: white solid, MS: m/z 340 ($M^{-1}$), mp 87.9–89.4° C. Anal. Calcd for $C_{18}H_{31}NO_5$: C, 63.32%; H, 9.15%; N, 4.10%. Found: C, 63.08%; H, 9.11%; N, 4.25%.

The less polar 12-epimer 6-[2-((3S)-(E)-3-Hydroxy-oct-1-enyl)-5-oxo-pyrrolidin-1-yloxy]-hexanoic acid: white waxy solid: MS: m/z 340 ($M^{-1}$), mp 54.7-60° C.).

Example 7

3-{3-[2-(3-Hydroxy-oct-1-ynyl)-5-oxo-pyrrolidin-1-yl]-propylsulfanyl}-propionic acid (29)

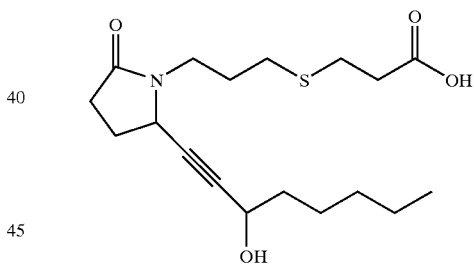

Step 1 and 2

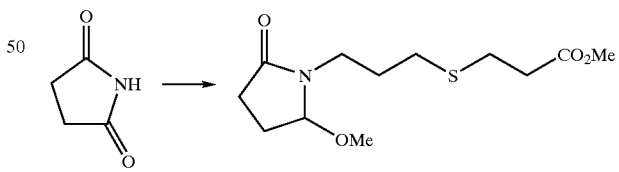

A dimethyl formamide (100 mL) suspension of potassium carbonate (5.9 g), succinimide (3.7 g), tetrabutylammonium iodide (500 mg), and methyl 7-chloro-4-thiaheptanoate (6.7 g) was stirred at ambient temperature for 44 h. The mixture was partitioned between water (400 mL) and 1:1 ether:hexane (4×100 mL) and dried over sodium sulfate. Following removal of the volatiles with a rotary evaporator, the crude mixture was subjected to silica gel chromatography. The desired product (4.7 g) was eluted with 3:2 hexane:ethyl acetate as an oil. The succinimide (4.4 g, 17 mmol) was dissolved in methanol,(100 mL) and cooled to –5° C. under argon. Sodium borohydride (911 mg, 24 mmol) was added in one portion and hydrochloric acid (2 M, methanol) was added dropwise over 3 h such that the internal temperature did not exceed +5° C. Additional sodium borohydride was added (275 mg, 7.2 mmol) and stirring continued for a total of 4 h and the pH was adjusted to 3–5 with more HCl/MeOH. The volatiles were removed from the mixture and the residue was treated with trimethyl orthoformate (15 mL) and p-toluene sulfonic acid hydrate (700 mg) and stirred at rt for about 18 h. The volatiles were removed with a rotary evaporator and the residue was subjected to silica gel chromatography. The desired 5-methoxylactam (1.14 g) was eluted with 3:1 hexane:acetone: ESMS: m/z M$^+$ with loss of OMe, 245.

Step 3, 4, and 5

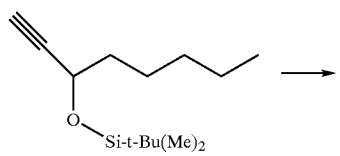

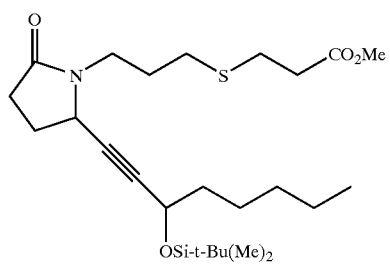

A tetrahydrofuran (50 mL) solution of 3-t-butyldimethylsilyloxy-1-octyne (4.0 g, 16.7 mmol) was cooled to −78° C. and treated with n-butyllithium (7.4 mL, 2.5 M hexane solution from Aldrich) and warmed to 0°. After 30 minutes, the solution was recooled to −78o and treated with tri-n-butyltin chloride (4.8 mL, Aldrich). The cooling bath was removed and the yellow solution was stirred at ambient temperature for 2 h. The mixture was partitioned between aqueous ammonium chloride and hexane (3×100 mL) and stored over sodium sulfate. The desired stannane (8.06 g, 15.2 mmol) was obtained following removal of the volatiles with a rotary evaporator and in vacuo (2 mmHg, rt, 2 h). The 5-methoxylactam (670 mg) and stannane (3.2 g) were dissolved in anhydrous dichloromethane (10 mL) and cooled to 0° C. under argon. Boron trifluoride etherate (1.2 mL, 9.6 mmol) was added in two portions and the resulting suspension was stirred at ambient temperature. After 18 h, the mixture was partitioned between pH 4 buffer and dichloromethane (2×50 mL), then stored over sodium sulfate. The desired alkyne (77 mg) was isolated by silica gel chromatography eluted with 3:2 hexane:ethyl acetate.

Step 6 and 7

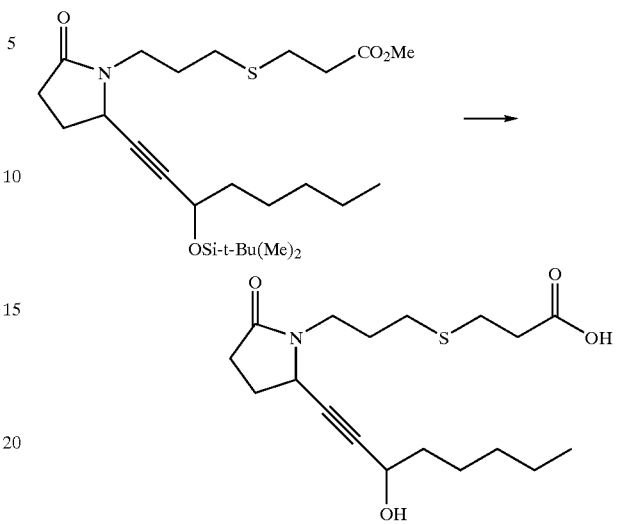

The silyl ether (77 mg) was dissolved in tetrahydrofuran (5 mL) and acetic acid (0.03 mL) at ambient temperature and treated with tetrabutylammonium fluoride (0.24 mL, 1 M THF solution, Aldrich) and stirred for 16 h. The solution was diluted with hexane (10 mL) and loaded onto a pad of silica. The alcohol (40 mg) eluted with 3:1 ethyl acetate:hexane and was suspended in 10 mL of 10 mM phosphate buffer (pH 6.5) at ambient temperature. The suspension was treated with Lipase type VII (500 mg from c. rugosa, Sigma) and stirred vigorously for 4–5 h. The mixture was diluted with ethyl acetate (15 mL) and acetic acid (0.5 mL)and loaded onto Celite. The filter cake was washed with ethyl acetate (40 mL). Following removal of the volatiles from the filtrate, the title acid was obtained as an oil (5.9 mg): $^1$H NMR (300 MHz, CDCl$_3$, partial spectrum) δ4.44–4.37 (m, 1H), 2.81 (t, J=6.8 Hz, 2H), 2.65 (t, J=7.1 Hz, 2H), MS: m/z (M$^{+1}$)356.

Example 8

The following are representative pharmaceutical formulations containing a compound of Formula I.

Tablet formulation
The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule formulation
The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

-continued

Suspension formulation
The following ingredients are mixed to
form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable formulation
The following ingredients are mixed to
form an injectable formulation.

| Ingredient | Amount |
| --- | --- |
| compound of this invention | 0.4 mg |
| sodium acetate buffer solution, 0.4 M | 2.0 mL |
| HCl (1 N) or NaOH (l N) | q.s. to suitable pH |
| water (distilled, sterile) | q.s. to 20 mL |

Example 9

Functional Activity of $EP_4$ (or $EP_2$) Receptor by a Luciferase Assay

Generation of Stably Transfected EP4-Luciferase Clones

Prostanoid receptor EP4 cDNA corresponding to the full-length coding sequence was subcloned into the appropriate sites of the mammalian expression vector pcDNA 3.1 (+)/Zeo (Invitrogen). In addition, the sequence containing CAMP responsive element (CRE) and luciferase gene was cloned to a pXPI vector. The co-transfection to the CHO cells with EP4R containing pcDNA and CRE-luciferase containing pXP1 were carried out with a DNA ratio of 5 to 1 by Fugene (Roche Molecular) in a F-12 media (Gibco) supplemented with 10% heat inactivated fetal Bovine Serum (Gibco). Thee days after the transfection, the culture was replace with fresh media containing Zeocin. The culture was maintained for one month until stable clones were generated.

c-AMP Dependent Luciferase Gene Assay

The functional activity of a EP4 agonistic ligand upon its binding to the receptor was measured by the production of intra-cellular c-AMP. Here the level of c-AMP was measured indirectly by the translation of .a reporter gene, luciferase in the EP4-luciferase clones. The cells of EP4-luciferase clone were subcultured in 200 ul of F12 (Gibco, BRL) media containing 10% FBS(Gibco, BRL), and 25 mM Hepes to 96-well plates (Packard) at the density of 40,000 cells/well. After an overnight culture at 37° C., 5% $CO_2$, 95% air, the culture media was removed in the next morning. The cells were washed twice with 100 ul of Hanks buffer, and re-furnished with 90 ul of F12 media containing 0.1% BSA. After pre-incubation of the culture for one and half to three hours at 37° C., 5% CO2, 95% air, 10 ul of compounds of interest at 10x of desired concentration were added to culture and the incubation at 37° C. was continued for another three hours. 0.1 uM of PGE2 as a full agonist control was routinely included to each assay to determine the maximal stimulation of luciferase mediated through EP4 receptor.

At the end of incubation, the culture media was dumped and blotted to dry. The plate was then ready to assay for luciferase.

Quantitation of Luciferase Activity

An assay kit, LucLite, purchased from Packard was used to quantitate luciferase activity. 30 minutes prior to end of incubation, LucLite substrate and substrate buffer (Packard) were allowed to equilibrate to room temperature. The substrate was dissolved in the substrate buffer and mixed by inversion. Equal volumes of Dulbecco's Phosphate Buffered Saline (DPBS, Gibco BRL) containing 1 MM $MgCl_2$ and 1 mM $CaCl_2$ were then mixed with the reconstituted substrate solution for use in the next step. 100 ul of the mixed solution was added to each well of the 96-well plate. The plate was shaken at 300 rpm on plate shaker for 3 min. The plate cover was removed and replaced with plate sealer (Packard) for counting in a scintillation counter. The EC50 of a compound was then determined by a four-parameter curvefit program of KaleidaGraph.

Example 10

Competitive Binding Assay of $[^3H]PGE_2$ to $rEP_1$, $rEP_2$, $rEP_3$ and $rEP_4$ Receptor Cell Culture and Transfections Stably transfected cells expressing EP3 were grown in F-12 media (GIBCO) supplemented with 10% heat inactivated certified Fetal Bovine Serum (GIBCO) and pelleted. Prostanoid receptor EP2 or EP4 cDNA corresponding to the full-length coding sequence was subcloned into the appropriate sites of the mammalian expresson vector pcDNA 3.1(+)/Zeo (Invitrogen). Transfection-scale quantities of the vector were prepared using the Qiagen Endo-Free Plasmid Maxi Kit and transfected into COS-7 cells using FuGene 6 (Roche Molecular) according to the manufacturer's instructions (Roche). COS-7 cells were grown in DMEM (GIBCO) supplemented with 10% heat inactivated certified Fetal Bovine Serum (GIBCO) and Gentamicin (GIBCO), and were harvested 72 hours after transfection. Cells were pelleted by centrifugation, washed with PBS (GIBCO), repelleted, then flash-frozen in dry-ice/Ethanol or used directly for membrane preparation.

Membrane Preparation

All procedures for membrane preparation were performed at 4° C. Prostanoid receptor-transfected COS-7 cells or stably transfected CHO cells were homogenized in assay buffers (see recipe, below) using a Polytron homogenizer (Brinkman) and centrifuged at 48,000×g for 30 minutes. Pellets were resuspended in assay buffer and resuspended by sonication using a Branson sonifier. Protein concentration was determined using the BioRad DC Protein Assay following the manufacturer's directions and stored at −80° C.

Prostanoid Receptor Binding Assays

Methods for competitive affinity binding assays of EP2, EP3 and EP4 were derived from those described in M. Abramovitz et al, "The utilization of recombinant prostanoid receptors to determine the affinities and selectivities of prostaglandins and related analogs" *Biochimica et Biophysica Acta* 1483 (2000) 285–293. Binding assays were performed in a final incubation volume of 0.2 mL in the following assay buffers: 20 mM HEPES, 1 mM EDTA, and 10 mM MgCl2 (pH 7.4) (EP3) or 10 mM MES, 10 mM MnCl2, and 1 mM EDTA_(pH to 6.0 with NaOH) (EP2 and EP4) and radioligand {2.25 nM (EP3) or 2.5 nM (EP2) $[^3H]$-$PGE_2$ (200 Ci/mmol, NEN)}. Reactions were initiated by addition of membrane protein (approximately 50 ug/reaction for EP3, 100 ug for EP2 and EP4). Dimethylsulfoxide (Sigma) concentration was kept constant at 1% (v/v) in all incubations, and compounds were assayed at final concentrations of 100 uM–0.3 nM. Non-specific binding was determined in the presence of 10 □M of nonradioactive PGE$_2$ (Cayman Chemical). Incubations were conducted for 60 minutes at 30° C. (EP3) or 45 minutes at 23° C. (EP2 and EP4). Incubations were terminated by rapid filtration through a 96-well Unifilter GF/B (Packard) (prewetted in 10 mM MES, 0.01% BSA, pH 6.0 for EP2) at 4° C. using a Filtermate 196 96-well semi-automated cell harvester (Packard). The filters were washed with 3–4 mL of wash buffer (20 mM HEPES pH 7.4 for EP3, 10 mM MES, 0.01% BSA, pH 6.0 for EP2 and EP4), dried for at least 1 hour at room temperature, and the residual radioactivity bound to the individual filters determined by scintillation counting with addition of 37.5 uL of Microscint 20 (Packard) using a Packard TopCount Microplate Scintillation Counter. Statistics of binding were determined using Prism v 3.0 software (GraphPad).

| Compound | EP$_1$, K$_i$ (nM) | EP$_2$, K$_i$ (nM) | EP$_3$, K$_i$ (nM) | EP$_4$, K$_i$ (nM) |
|---|---|---|---|---|
| 1 | >10,000 | 1,600 | 2,600 | 5 |
| 8 | NT | >10,000 | NT | NT |
| 10 | >10,000 | 66,000 | >10,000 | 7 |
| 14 | NT | 18,000 | NT | 90 |
| 15 | NT | 7,800 | 49,000 | 8 |
| 28 | NT | >10,000 | >10,000 | 60 |
| 29 | NT | NT | NT | NT |

NT = not tested

Example 11

Bone Mass Density Assay

The compounds of this invention may be evaluated for their effect on bone mass in ovariectomized rats.

Adult Sprague-Dawley or Wistar Hanover female rats are either sham operated or ovariectomized by Charles River. On receipt, rats are housed in pairs in an environmentally controlled room and acclimatized for at least one week. Animals are pair fed while were housed on site.

Test compound is administered subcutaneously once a day started from 20 days post surgery for 5 weeks in 10% EtOH/saline or 20 mM phosphate buffer.

Before the treatment and at the end of the treatment, rats are scanned using High Resolution Software Package on a Hologic QDR-4500 Bone Densitometer to measure the bone mineral density (BMD). Scans are then analyzed using regions of interest, as designated below: whole femur, proximal femur, femur diaphysis, distal femur, distal femur metaphysis, proximal tibia, proximal tibia metaphysis, L2–L4 vertebrae, L5 vertebrae.

For a verification of the effect of ovariectomy on bone mass, the sham and OVX of like vehicle groups are compared using a students t-test. The OVX groups are compared by one way analysis of variance (ANOA), followed by Fisher's LSD to compare each treatment group to vehicle when the overall effect was statistically significant. The data could be ranked prior to the above analysis and corresponding non-parametric analysis is performed (Wilcoxon rank-sum test or Kruskal-Wallis).

What is claimed is:

1. A compound represented by Formula I:

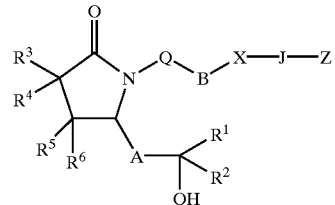

wherein:

Q is CH$_2$ or oxygen;

B is —CH$_2$—, —(CH$_2$)$_2$—, —(CH$_2$)$_3$—, —(CH$_2$)$_4$—, —(CH$_2$)$_5$—, —CH═CH—, —CH$_2$—CH═CH—, —CH═CH—CH$_2$—, or —CH$_2$—CH═CH—CH$_2$—, provided that when B is —CH═CH— or —CH═CH—CH$_2$—, then;

X is —NR$^a$— (where R$^a$ is hydrogen, halogen, (C$_1$–C$_6$) alkyl or (C$_1$–C$_6$)acyl), —O—, —S—, —SO— or —SO$_2$— or a single bond, provided that when X is a single bond, then Q is oxygen;

J is —(CR$^b$R$^c$)$_n$— (where n is an integer from 1 to 4, and R$^b$ and R$^c$ are both hydrogen or one or two of R$^b$ and R$^c$ are lower alkyl and the remainder are hydrogen, or R$^b$ and R$^c$ if attached to the same carbon atom form a C$_2$–C$_5$-polymethylene group) or —CH$_2$—CH═CH—;

A is —CH$_2$—CH$_2$—, —CH═CH—, or —C≡C—;

Z is CH$_2$OH, —C(O)OR', —C(O)NR'R", —C(O)NSO$_2$R', —P(C$_1$–C$_6$)alkyl(O)(OR'), (—PO(OR')$_2$, or tetrazol-5-yl; wherein R' and R" are independently from each other hydrogen or (C$_1$–C$_6$)alkyl;

n is 1, 2, 3 or 4;

R$^1$ is —(CH$_2$)$_p$R$^7$ or —(CH$_2$)$_q$OR$^8$, wherein R$^7$ and R$^8$ are each independently from each other (C$_1$–C$_6$)alkyl, halo(C$_1$–C$_6$)alkyl, (C$_3$–C$_8$)cycloalkyl, heterocyclyl, aryl or heteroaryl;

p and q are each independently from each other 0, 1, 2, 3, 4, or 5;

R$^2$ is hydrogen, (C$_1$–C$_6$)alkyl, (C$_1$–C$_6$)alkenyl, or (C$_1$–C$_6$)alkyl; and R$^3$, R$^4$, R$^5$ and R$^6$ are independently from each other hydrogen or (C$_1$–C$_6$)alkyl; or a pharmaceutically acceptable salt or solvate, prodrug, single isomer or racemic or non-racemic mixture of isomers thereof.

2. The compound of claim 1, wherein R$^1$ is —(CH$_2$)$_p$R$^7$ and R$^2$ is hydrogen.

3. The compound of claim 2, wherein R$^7$ is (C$_1$–C$_6$)alkyl or (C$_3$–C$_8$)cycloalkyl.

4. The compound of claim 3, wherein p is 4 and R$^7$ is methyl.

5. The compound of claim 2, wherein Z is COOH.

6. The compound of claim 5, wherein R$^7$ is aryl, heteroaryl or heterocyclyl.

7. The compound of claim 6, wherein R$^7$ is a phenyl optionally substituted with a substituent selected from the group consisting of alkyl, trifluoromethyl, halogen, —Y—R$^9$, —Y—OR$^9$ and —Y—C(O)R$^9$, wherein Y is a bond or a (C$_1$–C$_3$)alkylene group; and R$^9$ is (C$_1$–C$_6$)alkyl, aryl, heterocyclyl, heteroaryl, or heterocyclyl.

8. The compound of claim 7, wherein p is 0.

9. The compound of claim 8, wherein Q is —CH$_2$— and B is —CH$_2$— and X is —NH—, —O— or —S—.

10. The compound of claim 9, wherein J is —(CHR$^a$)$_3$— and one of R$^a$ is lower alkyl and the others are hydrogen.

11. The compound of claim 9, wherein J is CH$_2$—CH=CH—.

12. The compound of claim 10 wherein, R$^7$ is a phenyl optionally substituted with one or two substituents selected from the group consisting of alkyl, trifluoromethyl, halo, —Y—R$^9$ or —Y—OR$^9$, wherein Y is a bond and R$^9$ is (C$_1$–C$_6$)alkyl, halo optionally substituted phenyl.

13. The compound of claim 11 wherein, R$^7$ is a phenyl optionally substituted with one or two substituents selected from the group consisting of alkyl, trifluoromethyl, halo, —Y—R$^9$ or —Y—OR$^9$, wherein Y is a bond and R$^9$ is (C$_1$–C$_6$)alkyl, halo or optionally substituted phenyl.

14. The compound of claim 7, wherein p is 0.

15. The compound of claim 14, wherein Q is —CH$_2$— and B is —CH$_2$— and X is —NH—, —O— or —S—.

16. The compound of claim 15, wherein J is —(CHR$^a$)$_3$— and one of R$^a$ is lower alkyl and the others are hydrogen.

17. The compound of claim 15, wherein J is CH$_2$—CH=CH—.

18. The compound of claim 16 wherein, R$^7$ is a phenyl optionally substituted with one or two substituents selected from the group consisting of alkyl, trifluoromethyl, halo, —Y—R$^9$ or —Y—OR$^9$, wherein Y is a bond and R$^9$ is (C$_1$–C$_6$)alkyl, halo optionally substituted phenyl.

19. The compound of claim 17 wherein, R$^7$ is a phenyl optionally substituted with one or two substituents selected from the group consisting of alkyl, trifluoromethyl, halo, —Y—R$^9$ or —Y—OR$^9$, wherein Y is a bond and R$^9$ is (C$_1$–C$_6$)alkyl, halo optionally substituted phenyl.

20. The compound of claim 5 wherein:
Q is —CH$_2$—;
B is —CH$_2$—, —(CH$_2$)$_2$—, —(CH$_2$)$_3$—, —(CH$_2$)$_3$— or —(CH$_2$)$_4$—; and
X is —NH, —O—, —S—, —SO— or —SO$_2$—.

21. The compound of claim 20 wherein, R$^7$ is a phenyl optionally substituted with one or two substituents selected from the group consisting of alkyl, trifluoromethyl, halo, —Y—R$^9$ or —Y—OR$^9$, wherein Y is a bond and R$^9$ is (C$_1$–C$_6$)alkyl, halo or optionally substituted phenyl.

22. The compound of claim 21 wherein p is 0.

23. The compound of claim 21, wherein J is —(CHR$^a$)$_3$— and one of R$^a$ is lower alkyl and the others are hydrogen.

24. The compound of claim 21, wherein J is CH$_2$—CH=CH—.

25. The compound of claim 21, wherein J is —(CH$_2$)$_3$—.

26. The compound of claim 23 wherein p is 0 or 1.

27. The compound of claim 20 wherein A is CH=CH and R$^1$ is pentyl.

28. The compound of claim 20 wherein A is CH$_2$—CH$_2$— and R$^1$ is pentyl.

29. A pharmaceutical composition comprising a therapeutically effective amount of a compound of claim 1 in admixture with at least one suitable carrier diluent or excipient.

30. A method of treatment of a disease associated with bone disorders in a mammal treatable by administration of a selective EP$_4$ prostaglandin agonist comprising administration to the mammal a therapeutically effective amount of a compound of claim 1.

31. The method of claim 30 wherein the disease is osteoporosis.

32. A process for preparing a compound of claim 1 where R$^2$ is hydrogen, comprising:
reacting a compound of general formula d:

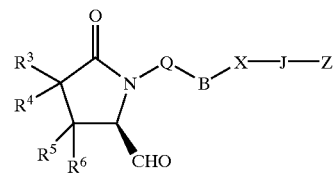

d wherein Q, B, X, J, Z, R$^3$, R$^4$, R$^5$, and R$^6$ are as defined in claim 1, with a phosphonate of general formula R$^1$—C(O)—CH$_2$PO(OCH$_3$)$_2$,
wherein R$^1$ is as defined in claim 1; followed by reduction and hydrolysis.

33. A process for preparing a compound of claim 1 wherein R$^2$ (C$_1$–C$_6$)alkyl, (C$_1$–C$_6$)alkenyl, or (C$_1$–C$_6$) alkynyl, comprising:
reacting a compound of general formula d:

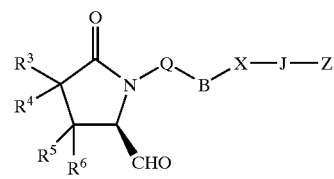

d wherein Q, B, X, J, Z, R$^3$, R$^4$, R$^5$, and R$^6$ are as defined in claim 1, with a phosphonate of general formula R$^1$—C(O)—CH$_2$PO(OCH$_3$)$_2$,
wherein R$^1$ is as defined in claim 1;
followed by reaction with an organometallic compound of formula R$^2$M, wherein M is a metal or magnesium halide followed by hydrolysis.

34. A compound of Formula II

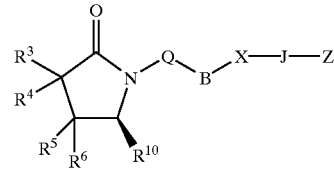

IV wherein:
Q is CH$_2$ or oxygen;
B is —CH$_2$—, —(CH$_2$)$_2$—, —(CH$_2$)$_3$—, —(CH$_2$)$_4$—, —(CH$_2$)$_5$—, —CH=CH—, —CH$_2$—CH=CH—, —CH=CH—CH$_2$—, or —CH$_2$—CH=CH—CH$_2$—, provided that when B is —CH=CH— or —CH=CH—CH$_2$—, then X is —NR$^a$—(where R$^a$ is hydrogen, halogen, (C$_1$–C$_6$) alkyl or (C$_1$–C$_6$)acyl), —O—, —S—, —SO— or —SO$_2$— or a single bond, provided that when X is a single bond, then Q is oxygen;

J is —(CR$^b$R$^c$)$_n$—(where n is an integer from 1 to 4, and R$^b$ and R$^c$ are both hydrogen or one or two of R$^b$ and R$^c$ are lower alkyl and the remainder are hydrogen, or R$^b$ and R$^c$ if attached to the same carbon atom form a C$_2$–C$_5$—polymethylene group) or —CH$_2$—

CH=CH—; PO(OR')$_2$, or tetrazol—5—yl; wherein R' and R" are independently from each other hydrogen or (C$_1$–C$_6$)alkyl;

R$^3$, R$^4$, R$^5$ and R$^6$ are independently from each other hydrogen or (C$_1$–C$_6$)alkyl;

Z is C(O)OR' where R' is hydrogen or (C$_1$–C$_6$)alkyl; and

R$^{10}$ is —CH$_2$OH, —CHO, —CH=CH—C(O)R$^1$; or a pharmaceutically acceptable salt, solvate or prodrug thereof.

35. A compound selected from the group consisting of:

4-[(2-{(2R)-2-[(1E,3S)-3-hydroxy-oct-1-enyl]-5-oxo-pyrrolidin-1-yl}ethyl)thio]butanoic acid methyl ester;

4-[(2-{(2R)-2-[(1E,3S)-3-hydroxy-oct-1-enyl]-5-oxo-pyrrolidin-1-yl}ethyl)thio]butanoic acid;

{4-[2[R-(3-hydroxy-oct-1E-enyl)5-oxo-pyrrolidin-1-yl]butylsulfanyl}acetic acid;

{4-[2[R-(1E-3S-3-hydroxy-oct-1-enyl)5-oxo-pyrrolidin-1-yl]butylsulfanyl}acetic acid;

{4-[(R)-2-((E)-3-hydroxy-oct-1-enyl)-5-oxo-pyrrolidin-1-yl]-butoxy}-acetic acid;

(4-{(R)-2-[(E)-3-Hydroxy-3-(5-trifluoromethyl-furan-2-yl)-propenyl]-5-oxo-pyrrolidin-1-yl}-butylsulfanyl)-acetic acid;

4-{2-[(R)-2-((S)-(E)-3-hydroxy-oct-1-enyl)-5-oxo-pyrrolidin-1-yl]-ethanesulfinyl}-butyric acid;

4-{2-[(R)-2-((S)-(E)-3-hydroxy-oct-1-enyl)-5-oxo-pyrrolidin-1-yl]-ethanesulfonyl}-butyric acid;

{(Z)-4-[(R)-2-((E)-3-hydroxy-oct-1-enyl)-5-oxo-pyrrolidin-1-yl]-but-2-enyloxy}-acetic acid;

{4-[(R)-2-((E)-(S)-3-Hydroxy-oct-1-enyl)-5-oxo-pyrrolidin-1-yl]-butoxy}-acetic acid;

(4-{(R)-2-[(S)-(E)-3-hydroxy-4-(3-trifluoromethyl-phenyl)-but-1-enyl]-5-oxo-pyrrolidin-1-yl}-butoxy)-acetic acid;

(4-{(R)-2-[(E)-3-hydroxy-3-(2'-methyl-biphenyl-3-yl)-propenyl]-5-oxo-pyrrolidin-1-yl}-butoxy)-acetic acid;

(4-{(R)-2-[(E)-3-(4'-chloro-biphenyl-3-yl)-3-hydroxy-propenyl]-5-oxo-pyrrolidin-1-yl}-butoxy)-acetic acid;

4-{2-[(R)-2-((E)-3-hydroxy-3-pentyl-oct-1-enyl)-5-oxo-pyrrolidin-1-yl]-ethylsulfanyl}-butyric acid;

4-{2-[(R)-2-((E)-3-hydroxy-3-methyl-oct-1-enyl)-5-oxo-pyrrolidin-1-yl]-ethylsulfanyl}-butyric acid;

4-[2-((S)-2-{(R)-3-[3-(3-Fluoro-phenoxy)-phenyl]-3-hydroxy-propyl}-5-oxo-pyrrolidin-1-yl)-ethylsulfanyl]-butyric acid;

4-[2-((S)-2-{(R)-3-[3-(4'-chloro-2'-methylphenyl)-phenyl]-3-hydroxy-propyl}-5-oxo-pyrrolidin-1-yl)-ethylsulfanyl]-butyric acid;

4-[2-((S)-2-{(S)-3-[3-(4'-chloro-2-methylphenyl)-phenyl]-3-hydroxy-propyl}-5-oxo-pyrrolidin-1-yl)-ethylsulfanyl]-butyric acid;

4-[2-((S)-2-{(R)-3-[3-(2',4'-difluorophenyl)-phenyl]-3-hydroxy-propyl}-5-oxo-pyrrolidin-1-yl)-ethylsulfanyl]-butyric acid;

4-[2-((S)-2-{(R)-3-[3-(4'-methoxy-2'-methyl-phenyl]-3-hydroxy-propyl}-5-oxo-pyrrolidin-1-yl)-ethylsulfanyl]-butyric acid;

4-{2-[(R)-2-((S)-(E)-3-hydroxy-oct-1-enyl)-5-oxo-pyrrolidin-1-yl]-ethylsulfanyl}-4-methyl-butyric acid;

4-{2-[(R)-2-((S)-(E)-3-hydroxy-oct-1-enyl)-5-oxo-pyrrolidin-1-yl]-ethylsulfanyl}-3-methyl-butyric acid;

4-{2-[(R)-2-((S)-(E)-3-hydroxy-oct-1-enyl)-5-oxo-pyrrolidin-1-yl]-ethylsulfanyl}-2-methyl-butyric acid;

4-{2-[(R)-2-((S)-(E)-3-hydroxy-oct-1-enyl)-5-oxo-pyrrolidin-1-yl]-ethylsulfanyl}-2-butenyric acid;

(1-{2-[(R)-2-((S)-(E)-3-hydroxy-oct-1-enyl)-5-oxo-pyrrolidin-1-yl]-ethylsulfanylmethyl}-cyclopropyl)-acetic acid;

5-{2-[(R)-2-((S)-(E)-3-hydroxy-oct-1-enyl)-5-oxo-pyrrolidin-1-yl]-ethylsulfanyl}-acetic acid;

3-{2-[(R)-2-((S)-(E)-3-hydroxy-oct-1-enyl)-5-oxo-pyrrolidin-1-yl]-ethylsulfanyl}-propionic acid;

5-{2-[(R)-2-((S)-(E)-3-hydroxy-oct-1-enyl)-5-oxo-pyrrolidin-1-yl]-ethylsulfanyl}-pentanoic acid;

6-[2-((S)-(E)-3-Hydroxy-oct-1-enyl)-5-oxo-pyrrolidin-1-yloxy]-hexanoic acid; and 3-{3-[2-(3-Hydroxy-oct-1-ynyl)-5-oxo-pyrrolidin-1-yl]-propylsulfanyl}-propionic acid.

\* \* \* \* \*